US011191893B2

(12) United States Patent
Capone et al.

(10) Patent No.: US 11,191,893 B2
(45) Date of Patent: Dec. 7, 2021

(54) SYSTEM AND METHOD FOR SYRINGE ENGAGEMENT WITH INJECTOR

(71) Applicant: BAYER HEALTHCARE LLC, Whippany, NJ (US)

(72) Inventors: Christopher Capone, Pittsburgh, PA (US); Jaroslaw Wlodarczyk, Lower Burrell, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 245 days.

(21) Appl. No.: 16/253,539

(22) Filed: Jan. 22, 2019

(65) Prior Publication Data

US 2019/0231975 A1 Aug. 1, 2019

Related U.S. Application Data

(60) Provisional application No. 62/624,384, filed on Jan. 31, 2018.

(51) Int. Cl.
*A61M 5/145* (2006.01)
*A61M 5/315* (2006.01)
(Continued)

(52) U.S. Cl.
CPC .... *A61M 5/14546* (2013.01); *A61M 5/14566* (2013.01); *A61M 5/007* (2013.01); *A61M 5/1408* (2013.01); *A61M 5/31511* (2013.01); *A61M 5/3221* (2013.01); *A61M 5/3234* (2013.01); *A61M 2005/323* (2013.01);
(Continued)

(58) Field of Classification Search
CPC .......... A61M 5/14546; A61M 5/14566; A61M 2005/14573; A61M 5/007; A61M 5/1456; A61M 2005/14553
See application file for complete search history.

(56) References Cited

U.S. PATENT DOCUMENTS 1,988,480 A 1/1935 Campkin
2,157,503 A 5/1939 Smith
(Continued)

FOREIGN PATENT DOCUMENTS

DE 69507018 T2 8/1999
DE 69416686 T2 10/1999
(Continued)

*Primary Examiner* — Emily L Schmidt
*Assistant Examiner* — Leah J Swanson
(74) *Attorney, Agent, or Firm* — Joseph L Kent; David Schramm; James R. Stevenson

(57) ABSTRACT

A fluid injector including an injector housing with at least one syringe port for receiving a syringe, and a locking mechanism associated with the at least one syringe port for securing the syringe within the at least one syringe port. The locking mechanism is configured for engaging at least one syringe retaining member of the syringe to releasably lock the syringe within the at least one syringe port. The at least one syringe retaining member rotationally guides the syringe into self-orienting alignment with the locking mechanism and is rotated by the locking mechanism into fully locked position after axial installation of the syringe into the at least one syringe port. The locking mechanism also axially ejects the syringe from the locking mechanism upon rotation of the syringe during removal.

20 Claims, 12 Drawing Sheets

(51) Int. Cl.
*A61M 5/00* (2006.01)
*A61M 5/14* (2006.01)
*A61M 5/32* (2006.01)

(52) U.S. Cl.
CPC .............. *A61M 2205/3306* (2013.01); *A61M 2205/3317* (2013.01); *A61M 2205/6072* (2013.01)

(56) References Cited

U.S. PATENT DOCUMENTS

| | | |
|---|---|---|
| 2,627,720 A | 2/1953 | Williams et al. |
| 2,734,504 A | 2/1956 | Crescas et al. |
| 2,946,331 A | 7/1960 | Jungst et al. |
| 2,956,563 A | 10/1960 | Sarnoff |
| 3,115,135 A | 12/1963 | Sarnoff |
| 3,348,545 A | 10/1967 | Sarnoff et al. |
| 3,395,704 A | 8/1968 | Frey et al. |
| 3,631,847 A | 1/1972 | James |
| 3,701,345 A | 10/1972 | Heilman |
| 3,752,145 A | 8/1973 | Runnells et al. |
| 3,812,843 A | 5/1974 | Wootten et al. |
| 3,880,138 A | 4/1975 | Wootten et al. |
| 4,006,736 A | 2/1977 | Kranys et al. |
| 4,150,672 A | 4/1979 | Martin et al. |
| 4,267,836 A | 5/1981 | Whitney et al. |
| 4,269,185 A | 5/1981 | Whitney et al. |
| 4,273,122 A | 6/1981 | Whitney et al. |
| 4,342,312 A | 8/1982 | Whitney et al. |
| 4,345,595 A | 8/1982 | Whitney et al. |
| 4,351,335 A | 9/1982 | Whitney et al. |
| 4,405,318 A | 9/1983 | Whitney et al. |
| 4,424,720 A | 1/1984 | Bucchianeri |
| 4,465,473 A | 8/1984 | Ruegg |
| 4,573,978 A | 3/1986 | Reilly |
| 4,634,431 A | 1/1987 | Whitney et al. |
| 4,636,198 A | 1/1987 | Stade |
| 4,677,980 A | 7/1987 | Reilly et al. |
| 4,695,271 A | 9/1987 | Goethel |
| 4,744,786 A | 5/1988 | Hooven |
| 4,753,638 A | 6/1988 | Peters |
| 4,854,324 A | 8/1989 | Hirschman et al. |
| 4,869,720 A | 9/1989 | Chernack |
| 4,936,833 A | 6/1990 | Sams |
| 4,966,601 A | 10/1990 | Draenert |
| 5,002,538 A | 3/1991 | Johnson |
| 5,007,904 A | 4/1991 | Densmore et al. |
| 5,098,386 A | 3/1992 | Smith |
| 5,178,609 A | 1/1993 | Ishikawa |
| 5,209,731 A | 5/1993 | Sterman et al. |
| 5,219,099 A | 6/1993 | Spence et al. |
| 5,269,762 A | 12/1993 | Armbruster et al. |
| 5,279,569 A | 1/1994 | Neer et al. |
| 5,300,031 A | 4/1994 | Neer et al. |
| 5,383,858 A | 1/1995 | Reilly et al. |
| 5,451,221 A | 9/1995 | Cho et al. |
| 5,456,669 A | 10/1995 | Neer et al. |
| 5,520,653 A | 5/1996 | Reilly et al. |
| 5,535,746 A | 7/1996 | Hoover et al. |
| 5,779,675 A | 7/1998 | Reilly et al. |
| 5,782,815 A | 7/1998 | Yanai et al. |
| 5,792,102 A | 8/1998 | Mueller-Spaeth |
| 5,848,993 A | 12/1998 | Tanhehco et al. |
| 5,873,861 A | 2/1999 | Hitchins et al. |
| 5,944,694 A | 8/1999 | Hitchins et al. |
| 5,947,929 A | 9/1999 | Trull |
| 5,947,935 A | 9/1999 | Kazousky et al. |
| 6,315,758 B1 | 11/2001 | Neer et al. |
| 6,336,913 B1 | 1/2002 | Spohn et al. |
| 6,368,307 B1 | 4/2002 | Ziemba et al. |
| 6,432,089 B1 | 8/2002 | Kakimi et al. |
| 6,520,930 B2 | 2/2003 | Critchlow et al. |
| 6,620,134 B1 | 9/2003 | Trombley, III et al. |
| 6,652,489 B2 | 11/2003 | Trocki et al. |
| 6,659,979 B2 | 12/2003 | Neer et al. |
| 6,716,195 B2 | 4/2004 | Nolan et al. |
| 6,733,477 B2 | 5/2004 | Cowan et al. |
| 6,743,202 B2 | 6/2004 | Hirschman et al. |
| 6,808,507 B2 | 10/2004 | Roser |
| 6,958,053 B1 | 10/2005 | Reilly |
| 7,273,477 B2 | 9/2007 | Spohn et al. |
| 7,361,156 B2 | 4/2008 | Joyce et al. |
| 7,393,341 B2 | 7/2008 | Nemoto |
| 7,419,478 B1 | 9/2008 | Reilly et al. |
| 7,462,166 B2 | 12/2008 | Kowan et al. |
| 7,497,843 B1 | 3/2009 | Castillo et al. |
| 7,553,294 B2 | 6/2009 | Lazzaro et al. |
| 7,563,249 B2 | 7/2009 | Schriver et al. |
| 7,666,169 B2 | 2/2010 | Cowan et al. |
| 7,674,244 B2 | 3/2010 | Kalafut et al. |
| 7,682,345 B2 | 3/2010 | Savage |
| 7,691,085 B2 | 4/2010 | Dedig et al. |
| 7,846,136 B2 | 12/2010 | Witowski |
| 8,012,125 B1 | 9/2011 | Fago et al. |
| 8,038,651 B2 | 10/2011 | Keller |
| 8,133,203 B2 | 3/2012 | Hack et al. |
| 8,366,670 B2 | 2/2013 | Neer et al. |
| 8,439,876 B2 | 5/2013 | Spohn et al. |
| 8,572,834 B2 | 11/2013 | Cude |
| 8,632,506 B2 | 1/2014 | Steenfeldt-Jensen et al. |
| 8,721,596 B2 | 5/2014 | Trocki et al. |
| 9,173,995 B1 | 11/2015 | Tucker et al. |
| 9,474,857 B2 | 10/2016 | Riley et al. |
| 9,597,706 B2 | 3/2017 | Burns |
| 9,700,670 B2 | 7/2017 | Tucker et al. |
| 2001/0047153 A1 | 11/2001 | Trocki et al. |
| 2001/0047162 A1 | 11/2001 | Yugari |
| 2002/0128607 A1 | 9/2002 | Haury et al. |
| 2004/0064041 A1 | 4/2004 | Lazzaro et al. |
| 2004/0122370 A1 | 6/2004 | Joyce et al. |
| 2005/0171477 A1 | 8/2005 | Rubin et al. |
| 2007/0219508 A1 | 9/2007 | Bisegna et al. |
| 2009/0112087 A1 | 4/2009 | Fago |
| 2011/0106015 A1 | 5/2011 | Liscio et al. |
| 2011/0208123 A1 | 8/2011 | Gray et al. |
| 2012/0016234 A1 | 1/2012 | Nemoto et al. |
| 2012/0265143 A1 | 10/2012 | Krumme et al. |
| 2013/0274655 A1 | 10/2013 | Jennings et al. |
| 2013/0281940 A1 | 10/2013 | Gelblum et al. |
| 2013/0340608 A1 | 12/2013 | Yamamoto |
| 2016/0114099 A1* | 4/2016 | Tucker .............. A61M 5/14566 604/154 |
| 2016/0354537 A1* | 12/2016 | Jozwik .............. A61M 5/31578 |

FOREIGN PATENT DOCUMENTS

| | | |
|---|---|---|
| DE | 69527281 T2 | 1/2003 |
| DE | 202004005433 U1 | 7/2004 |
| DE | 102004032970 A1 | 2/2006 |
| EP | 0143895 A1 | 6/1985 |
| EP | 0346950 A2 | 12/1989 |
| EP | 0362484 A2 | 4/1990 |
| EP | 0482677 B1 | 4/1998 |
| EP | 0893133 B1 | 11/2002 |
| EP | 1416994 A1 | 5/2004 |
| EP | 1188669 B1 | 8/2004 |
| EP | 1465101 A2 | 10/2004 |
| EP | 1281408 B1 | 11/2004 |
| EP | 1484071 A1 | 12/2004 |
| EP | 1512423 A1 | 3/2005 |
| EP | 1531889 A1 | 5/2005 |
| EP | 1563859 A1 | 8/2005 |
| EP | 1588728 A1 | 10/2005 |
| EP | 1596908 A1 | 11/2005 |
| EP | 1642606 A1 | 4/2006 |
| EP | 1647291 A1 | 4/2006 |
| EP | 1681069 A1 | 7/2006 |
| EP | 1688157 A1 | 8/2006 |
| EP | 1703924 A1 | 9/2006 |
| EP | 1723977 A1 | 11/2006 |
| EP | 1732093 A1 | 12/2006 |
| EP | 1736189 A1 | 12/2006 |
| EP | 1767233 A1 | 3/2007 |
| EP | 1782853 A1 | 5/2007 |

(56) References Cited

FOREIGN PATENT DOCUMENTS

| | | |
|---|---|---|
| EP | 1820523 A1 | 8/2007 |
| EP | 1820524 A1 | 8/2007 |
| EP | 1825875 A1 | 8/2007 |
| EP | 1825876 A1 | 8/2007 |
| EP | 1825877 A1 | 8/2007 |
| EP | 1827535 A2 | 9/2007 |
| EP | 1896100 A2 | 3/2008 |
| EP | 1932556 A1 | 6/2008 |
| EP | 1888218 B1 | 12/2008 |
| EP | 1486219 B1 | 4/2009 |
| EP | 2043708 A1 | 4/2009 |
| EP | 2015800 A4 | 5/2009 |
| EP | 2055332 A1 | 5/2009 |
| EP | 1847285 B1 | 9/2009 |
| EP | 1670522 B1 | 11/2009 |
| EP | 2156857 A2 | 2/2010 |
| EP | 2187993 A1 | 5/2010 |
| EP | 2227274 A1 | 9/2010 |
| EP | 2227276 A1 | 9/2010 |
| EP | 2240219 A2 | 10/2010 |
| EP | 2244766 A1 | 11/2010 |
| EP | 2253348 A1 | 11/2010 |
| EP | 2315148 A1 | 4/2011 |
| EP | 2025356 B1 | 5/2011 |
| EP | 2318966 A2 | 5/2011 |
| EP | 2331175 A1 | 6/2011 |
| EP | 2341456 A1 | 7/2011 |
| EP | 2347359 A2 | 7/2011 |
| EP | 2353118 A1 | 8/2011 |
| EP | 2361647 A1 | 8/2011 |
| EP | 2362791 A2 | 9/2011 |
| EP | 2376146 A2 | 10/2011 |
| EP | 2384778 A1 | 11/2011 |
| EP | 2409720 A1 | 1/2012 |
| EP | 2411071 A1 | 2/2012 |
| EP | 2416821 A1 | 2/2012 |
| EP | 2427234 A1 | 3/2012 |
| EP | 2429614 A2 | 3/2012 |
| EP | 2227275 B1 | 6/2012 |
| EP | 2464402 A2 | 6/2012 |
| EP | 2337595 B1 | 7/2012 |
| EP | 2481430 A1 | 8/2012 |
| EP | 2485790 A1 | 8/2012 |
| EP | 2316509 B1 | 10/2012 |
| EP | 2363158 B1 | 11/2012 |
| EP | 2536449 A1 | 12/2012 |
| EP | 1938853 B1 | 1/2013 |
| EP | 2222358 B1 | 1/2013 |
| EP | 2275155 B1 | 4/2013 |
| EP | 2316507 B1 | 4/2013 |
| EP | 2316506 B1 | 5/2013 |
| EP | 2359883 B1 | 5/2013 |
| EP | 2229199 B1 | 6/2013 |
| EP | 2416824 B1 | 6/2013 |
| EP | 2618870 A2 | 7/2013 |
| EP | 2621553 A2 | 8/2013 |
| EP | 2628496 A1 | 8/2013 |
| EP | 2363160 B1 | 9/2013 |
| EP | 2251053 B1 | 10/2013 |
| EP | 2643035 A2 | 10/2013 |
| EP | 2654843 A1 | 10/2013 |
| EP | 2665501 A1 | 11/2013 |
| EP | 1716884 B1 | 12/2013 |
| EP | 2286855 B1 | 12/2013 |
| EP | 2520318 B1 | 12/2013 |
| EP | 2671603 A1 | 12/2013 |
| EP | 2686040 A1 | 1/2014 |
| EP | 2692375 A1 | 2/2014 |
| EP | 2185227 B1 | 3/2014 |
| EP | 2707824 A2 | 3/2014 |
| EP | 2732393 A2 | 5/2014 |
| EP | 2734253 A1 | 5/2014 |
| GB | 848204 A | 9/1960 |
| GB | 1049263 A | 11/1966 |
| GB | 1576733 A | 10/1980 |
| GB | 2486690 A | 6/2012 |
| GB | 2501897 A | 11/2013 |
| JP | 2006512106 A | 4/2006 |
| JP | 2009540995 A | 11/2009 |
| JP | 2010214048 A | 9/2010 |
| JP | 4833984 B2 | 12/2011 |
| JP | 2012106029 A | 6/2012 |
| JP | 2012120934 A | 6/2012 |
| JP | 4965582 B2 | 7/2012 |
| JP | 2014004480 A | 1/2014 |
| JP | 5436897 B2 | 3/2014 |
| JP | 5518844 B2 | 6/2014 |
| WO | 0012157 A1 | 3/2000 |
| WO | 0012158 A1 | 3/2000 |
| WO | 2004004812 A1 | 1/2004 |
| WO | 2007130061 A1 | 11/2007 |
| WO | 2008009645 A1 | 1/2008 |
| WO | 2009036496 A2 | 3/2009 |
| WO | 2011131778 A1 | 10/2011 |
| WO | 2011131783 A2 | 10/2011 |
| WO | 2012124028 A1 | 9/2012 |
| WO | 2012155035 A1 | 11/2012 |
| WO | 2013149979 A1 | 10/2013 |

* cited by examiner

SYSTEM AND METHOD FOR SYRINGE ENGAGEMENT WITH INJECTOR

CROSS REFERENCE TO RELATED APPLICATIONS

This application claims priority to U.S. Provisional Application No. 62/624,384, filed 31 Jan. 2018, the disclosure of which is incorporated herein in its entirety.

BACKGROUND OF THE DISCLOSURE

Field of the Disclosure

The present disclosure relates generally to a system including a front-loading syringe for use with a fluid injector and a locking mechanism for engaging and disengaging the syringe with the fluid injector, and, further, to a method for engaging the syringe with the injector and disengaging the syringe from the injector.

Description of Related Art

In many medical diagnostic and therapeutic procedures, a medical practitioner, such as a physician, injects a patient with one or more medical fluids. In recent years, a number of injector-actuated syringes and fluid injectors for pressurized injection of fluids, such as a contrast solution (often referred to simply as "contrast"), a flushing agent, such as saline, and other medical fluids have been developed for use in procedures such as angiography, computed tomography (CT), ultrasound, magnetic resonance imaging (MRI), positron emission tomography (PET), and other imaging procedures. In general, these fluid injectors are designed to deliver a preset amount of fluid at a preset flow rate.

Various front-loading connection interfaces have been developed to facilitate the loading and removal of the syringe to and from the fluid injector. In some examples, the syringe having a retention feature is inserted into a syringe port on the fluid injector by aligning the syringe with a corresponding locking feature provided on the fluid injector. It is often necessary for the medical practitioner to align the retention feature of the syringe with the corresponding locking feature on the fluid injector before the syringe can be loaded onto the injector. In some cases, there are only one or two orientations in which the syringe can be aligned with the locking feature on the injector, such as shown in U.S. Pat. No. 5,383,858. In these syringes, the operator must rotate the syringe to find an alignment that allows the syringe to engage with the fluid injector. It is then necessary for the operator to rotate the syringe relative to the locking feature to create a strong enough engagement for operation of the injector. In another example disclosed in U.S. Pat. No. 6,652,489, there is no need to rotationally align the syringe or to rotate the syringe for installation or engagement. To remove the syringe, the operator must rotate the syringe at least 45 degrees, and more commonly 90 degrees, about its longitudinal axis. After rotation, the operator must pull the syringe out of the injector. In some examples, the operator must pull on the syringe at the same time while turning the syringe.

There is a need in the art for an improved connection interface that allows the operator to more easily engage and disengage the syringe to and from the fluid injector to relieve the operator of the effort of simultaneously pushing or pulling and rotating the syringe. There is a further need in the art for reducing or eliminating the need for the operator to rotationally align the syringe with the fluid injector during engagement of the syringe with the fluid injector. While various syringe connection interfaces and methods are known in the medical field, improved connection interfaces between the syringe and the fluid injector and methods for loading and removing the syringe to and from the fluid injector continue to be in demand.

SUMMARY OF DISCLOSURE

In view of the disadvantages of the existing connection interfaces between the syringe and the fluid injector, there is a need in the art for an improved connection interface between the syringe and the fluid injector that overcomes the deficiencies of the prior art. There is an additional need for improved methods for engaging and disengaging the syringe to and from the fluid injector so that the syringe does not have to be rotationally aligned about its longitudinal axis relative to the fluid injector to allow easy loading or removal of the syringe to and from the fluid injector.

In some examples of the present disclosure, a medical fluid injector is described. The medical fluid injector may comprise an injector housing, at least one syringe port in the injector housing for receiving a proximal portion of a syringe, and a locking mechanism associated with the at least one syringe port for releasably locking the syringe within the at least one syringe port by releasably engaging at least one syringe retaining member of the syringe. The locking mechanism may comprise a locking ring rotatable between a first locked position and a second insertion/removal position for insertion or removal of the syringe from the locking mechanism, a biasing mechanism, such as a spring, for biasing the locking ring in the first locked position, and at least one guide second member on the locking ring, the at least one guide second member having a ramp surface for interacting with the at least one syringe retaining member of the syringe to rotate the locking ring from the first locked position to the second insertion/removal position as the syringe is inserted into the at least one syringe port. The at least one guide second member on the locking ring may interact with the at least one syringe retaining member of the syringe to rotate the locking ring from the first locked position to the second insertion/removal position when the syringe is rotated while in a locked position in the locking mechanism. A ramp surface of the at least one second guide member may interact with the at least one syringe retaining member of the syringe to axially eject the syringe from the locked position when the locking ring is rotated into the second insertion/removal position.

The locking ring of the medical fluid injector may further include a stop surface at least partially extending from the proximal end of the ramp surface to the distal surface of the locking ring, wherein the stop surface prevents rotation of the syringe relative to the locking mechanism when the syringe is locked within the mechanism. In certain aspects, the at least one syringe port further may comprise a sidewall having a plurality of recesses and at least one first guide member extending radially inward from the side wall and positioned between each adjacent recesses of the plurality of recesses. For example, the at least one first guide member may comprise one or more guiding surfaces for guiding the at least one syringe retaining member into self-orienting alignment with the locking ring. The at least one first guide member may comprise a first guiding ramp and a second guiding ramp, wherein the first guiding ramp and the second guiding ramp are inclined toward a first adjacent recess and a second adjacent recess, respectively, on each side of the at least one first guide member. The at least one first guide member may have a proximal surface for abutting against a base surface the at least one syringe retaining member when the syringe is locked within the locking mechanism to prevent distal movement of the syringe when locked in the locking mechanism.

Other embodiments of the present disclosure relate to a fluid injector, where the fluid injector may comprise an injector housing with at least one syringe port for receiving a syringe. The injector housing may include a locking mechanism associated with the at least one syringe port for securing the syringe within the at least one syringe port. The locking mechanism may be configured for engaging at least one syringe retaining member of the syringe to releasably lock the syringe within the at least one syringe port. The at least one syringe retaining member may rotationally guide the syringe into self-orienting alignment with the locking mechanism and axially ejects the syringe from the locking mechanism upon rotation of the syringe. The locking mechanism may comprise a housing having a central opening configured to receive the proximal end of the syringe, a locking ring disposed within the housing, the locking ring rotatable between a first locked position and a second insertion/removal position with rotation of the syringe about a longitudinal axis; and a biasing mechanism for biasing the locking ring in the first locked position. The biasing mechanism may be a spring.

In other embodiments, the present disclosure provides a fluid injection apparatus. The fluid injection apparatus may have at least one syringe comprising a barrel with a distal end, a proximal end, and a sidewall extending substantially circumferentially between the distal end and the proximal end along a longitudinal axis, the barrel having at least one syringe retaining member protruding radially outward from the proximal end. The fluid injection apparatus may also have an injector comprising an injector housing with at least one syringe port for receiving the at least one syringe, and a locking mechanism associated with the at least one syringe port for securing the at least one syringe within the at least one syringe port. The locking mechanism may be configured for engaging the at least one syringe retaining member of the at least one syringe to releasably lock the at least one syringe within the at least one syringe port. The at least one syringe retaining member may rotationally guide the at least one syringe into self-orienting alignment with the locking mechanism and axially eject the at least one syringe from the locking mechanism upon rotation of the at least one syringe. The locking mechanism may further comprise at least one sensor for detecting an angular position of the locking ring based on orientation of a sensor pickup on the locking ring relative to the at least one sensor. The at least one sensor may be an optical sensor, a Hall Effect sensor, or a combination thereof. The at least one syringe port may further comprise a sidewall having a plurality of recesses and at least one first guide member positioned between each adjacent recesses of the plurality of recesses. The at least one first guide member may comprise one or more guiding surfaces for guiding the at least one syringe retaining member into the self-orienting alignment with the locking ring.

In other examples of the present disclosure, the locking mechanism may have a housing having a central opening configured to receive the proximal end of the at least one syringe, a locking ring disposed within the housing, the locking ring rotatable between a first position and a second position with rotation of the at least one syringe about the longitudinal axis, and a biasing mechanism for biasing the locking ring in the first position. The biasing mechanism may be a spring, such as a constant-force spring. The locking mechanism may have at least one sensor for detecting an angular position of the locking ring based on the orientation of a sensor pickup on the locking ring relative to the at least one sensor. The at least one sensor may be an optical sensor, a Hall Effect sensor, or a combination thereof. The sensor pickup may be a magnet. The at least one syringe retaining member may extend about at least a portion of a circumference of the syringe barrel. The at least one syringe retaining member may be a plurality of syringe retaining members spaced apart evenly about the circumference of the syringe barrel. The at least one syringe retaining member may have a substantially triangular shape with a base surface, a side surface, and a guide surface. The guide surface may be linear or curvilinear. The guide surface may be continuous or discontinuous.

Various aspects of the fluid injection apparatus are disclosed in one or more of the following clauses:

Clause 1. A medical fluid injector comprising: an injector housing; at least one syringe port in the injector housing for receiving a proximal portion of a syringe; and a locking mechanism associated with the at least one syringe port for releasably locking the syringe within the at least one syringe port by releasably engaging at least one syringe retaining member of the syringe, the locking mechanism comprising: a locking ring rotatable between a first locked position and a second insertion/removal position for insertion or removal of the syringe from the locking mechanism; a biasing mechanism for biasing the locking ring in the first locked position; and at least one guide second member on the locking ring, the at least one guide second member having a ramp surface for interacting with the at least one syringe retaining member of the syringe to rotate the locking ring from the first locked position to the second insertion/removal position as the syringe is inserted into the at least one syringe port.

Clause 2. The medical fluid injector of clause 1, wherein the at least one guide second member on the locking ring interacts with the at least one syringe retaining member of the syringe to rotate the locking ring from the first locked position to the second insertion/removal position when the syringe is rotated while in a locked position in the locking mechanism.

Clause 3. The medical fluid injector of clause 2, wherein a ramp surface of the at least one second guide member interacts with the at least one syringe retaining member of the syringe to axially eject the syringe from the locked position when the locking ring is rotated into the second insertion/removal position.

Clause 4. The medical fluid injector of any of clauses 1 to 3, wherein the locking ring further comprises a stop surface at least partially extending from the proximal end of the ramp surface to the distal surface of the locking ring, wherein the stop surface prevents rotation of the syringe relative to the locking mechanism when the syringe is locked within the mechanism.

Clause 5. The medical fluid injector of any of clauses 1 to 4, wherein the at least one syringe port further comprises a sidewall having a plurality of recesses and at least one first guide member extending radially inward from the side wall and positioned between each adjacent recesses of the plurality of recesses.

Clause 6. The medical fluid injector of clause 5, wherein the at least one first guide member comprises one or more guiding surfaces for guiding the at least one syringe retaining member into self-orienting alignment with the locking ring.

Clause 7. The medical fluid injector of clause 5 or 6, wherein the at least one first guide member comprises a first guiding ramp and a second guiding ramp, wherein the first guiding ramp and the second guiding ramp are inclined toward a first adjacent recess and a second adjacent recess, respectively, on each side of the at least one first guide member.

Clause 8. The medical fluid injector of any of clauses 5 to 7, wherein the at least one first guide member has a proximal surface for abutting against a base surface the at least one syringe retaining member when the syringe is locked within the locking mechanism to prevent distal movement of the syringe when locked in the locking mechanism.

Clause 9. The medical fluid injector of any of clauses 1 to 8, wherein the biasing mechanism is a spring.

Clause 10. The medical fluid injector of any of clauses 1 to 9, wherein the locking mechanism further comprises at least one sensor for detecting an angular position of the locking ring based on an orientation of a sensor pickup on the locking ring relative to the at least one sensor.

Clause 11. The medical fluid injector of clause 10, wherein the at least one sensor is an optical sensor, a Hall Effect sensor, or a combination thereof.

Clause 12. The medical fluid injector of clause 10 or 11, wherein the sensor pickup is a magnet.

Clause 13. The medical fluid injector of any of clauses 1 to 12, wherein the at least one injector port comprises a barcode reader system for reading at least one identification tag on the proximal portion of the syringe.

Clause 14. A fluid injector comprising an injector housing with at least one syringe port for receiving a syringe, the injector housing comprising a locking mechanism associated with the at least one syringe port for securing the syringe within the at least one syringe port, the locking mechanism configured for engaging at least one syringe retaining member of the syringe to releasably lock the syringe within the at least one syringe port, wherein the at least one syringe retaining member rotationally guides the syringe into self-orienting alignment with the locking mechanism and axially ejects the syringe from the locking mechanism upon rotation of the syringe.

Clause 15. The fluid injector of clause 14, wherein the locking mechanism comprises a housing having a central opening configured to receive the proximal end of the syringe; a locking ring disposed within the housing, the locking ring rotatable between a first locked position and a second insertion/removal position with rotation of the syringe about a longitudinal axis; and a biasing mechanism for biasing the locking ring in the first locked position.

Clause 16. The fluid injector of clause 15, wherein the biasing mechanism is a spring.

Clause 17. The fluid injector of any of clauses 14 to 16, wherein the locking mechanism further comprising at least one sensor for detecting an angular position of the locking ring based on orientation of a sensor pickup on the locking ring relative to the at least one sensor.

Clause 18. The fluid injector of clause 17, wherein the at least one sensor is an optical sensor, a Hall Effect sensor, or a combination thereof.

Clause 19. The fluid injector of any of clauses 14 to 18, wherein the at least one syringe port further comprises a sidewall having a plurality of recesses and at least one first guide member positioned between each adjacent recesses of the plurality of recesses.

Clause 20. The fluid injector of clause 19, wherein the at least one first guide member comprises one or more guiding surfaces for guiding the at least one syringe retaining member into self-orienting alignment with the locking ring.

These and other features and characteristics of syringes, syringe connection interfaces, and systems having syringes and/or syringe connection interfaces, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only.

DETAILED DESCRIPTION

Figure 1:
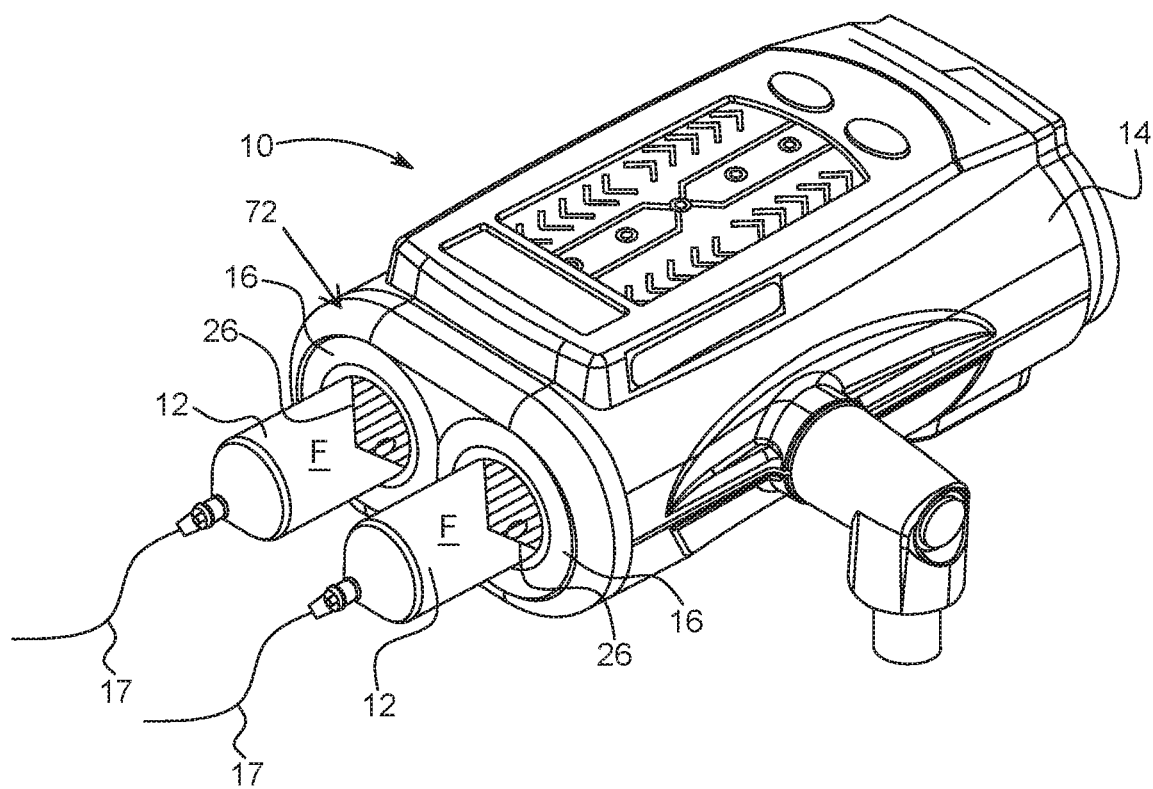
FIG. 1 is a perspective view of a fluid delivery system having a fluid injector and a syringe according to an example of the present disclosure.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. As used in the specification and the claims, the singular form of "a", "an", and "the" include plural referents unless the context clearly dictates otherwise.

When used in relation to a syringe and/or a plunger, the term "proximal" refers to a portion of a syringe and/or a plunger nearest a fluid injector when a syringe and/or a plunger is oriented for connecting to a fluid injector. The term "distal" refers to a portion of a syringe and/or a plunger farthest away from a fluid injector when a syringe and/or a plunger is oriented for connecting to a fluid injector. The term "radial" refers to a direction in a cross-sectional plane normal to a longitudinal axis of a syringe, a plunger, and/or a piston extending between proximal and distal ends. The term "circumferential" refers to a direction around an inner or outer surface of a sidewall of a syringe, a plunger, and/or a piston. The term "axial" refers to a direction along a longitudinal axis of a syringe, a piston, and/or a piston extending between the proximal and distal ends. The term "self-orienting" means that a piston head or a plunger orients itself to a correct orientation relative to a plunger or piston head, respectively, without a rotational effort by a technician or a fluid injector. The term "curvilinear" refers to a shape of a surface that has one or more curved lines, one or more straight lines with one or more curved lines, and/or one or more straight line segments arranged non-linearly.

It is to be understood that the disclosure may assume alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the examples disclosed herein are not to be considered as limiting.

Referring to the drawings in which like reference characters refer to like parts throughout the several views thereof, the present disclosure is generally directed to a syringe and a connection interface for connecting the syringe to the fluid injector.

With reference to FIG. 1, a fluid injector 10 (hereinafter referred to as "injector 10"), such as an automated or powered fluid injector, is adapted to interface with and actuate one or more syringes 12 (hereinafter referred to as "syringe 12"), which may be filed with a fluid F, such as contrast media, saline solution, or any desired medical fluid. The injector 10 may be used during a medical procedure to inject the medical fluid into the body of a patient by driving a plunger 26 of the syringe 12 with a linear actuator or a piston element. The injector 10 may be a multi-syringe injector, wherein several syringes 12 may be oriented in a side-by-side relationship and are separately actuated by respective linear actuators or piston elements associated with the injector 10. In examples with two syringes arranged in a side-by-side or other relationship and filled with two different fluids, the injector 10 may be configured to deliver fluid from one or both of the syringes 12.

The injector 10 may be enclosed within a housing 14 formed from a suitable structural material, such as plastic or metal. The housing 14 may be of various shapes and sizes depending on the desired application. For example, the injector 10 may be a free-standing structure configured to be placed on the floor or may be a smaller design for placement on a suitable table or support frame. The injector 10 includes one or more syringe ports 16 for connecting the syringes 12 to respective piston elements. The one or more syringe ports 16 may be located on a face plate 72 of the injector. As will be described hereinafter, in some examples, the syringe 12 includes one or more syringe retaining members configured for retaining the syringe 12 within the syringe port 16 of the injector 10. The one or more syringe retaining members is configured to operatively engage a locking mechanism of the injector 10 to facilitate loading or removal of the syringe 12 to and from the injector 10, as described herein. The syringe retaining member and the locking mechanism together define a connection interface for connecting the syringe 12 to the injector 10.

A fluid path set 17 may be fluidly connected with the syringe 12 for delivering fluid F from the syringe 12 to a catheter (not shown) inserted into a patient at a vascular access site. Fluid flow from the syringe 12 may be regulated by a fluid control module (not shown). The fluid control module may regulate the delivery of the saline solution and contrast to the patient by controlling the speed of the corresponding injector piston (and hence the speed of the syringe plungers) based on user selected injection parameters, such as injection flow rate, duration, total injection volume, and ratio of contrast media and saline.

Figure 2A:
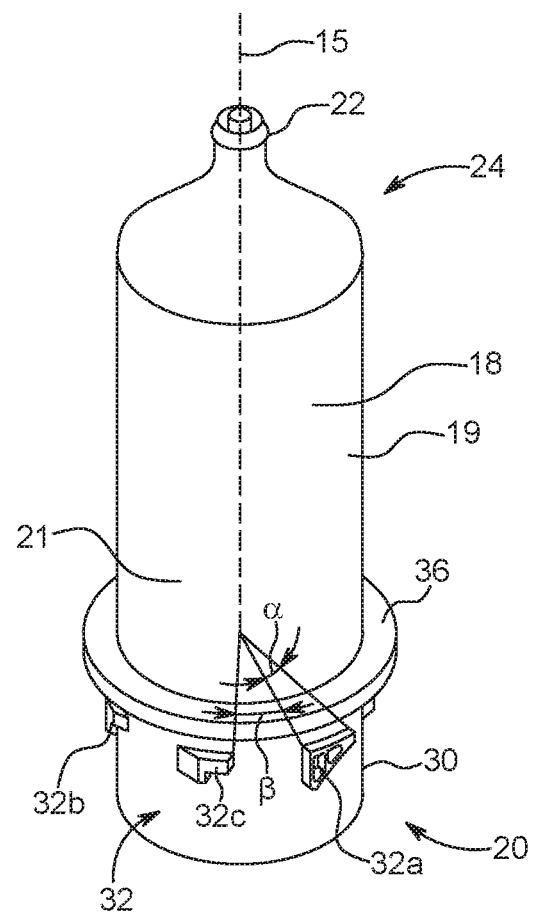
FIG. 2A is a perspective view of a syringe according to one example of the present disclosure.

Having described the general structure and function of the injector 10, the syringe 12 will now be discussed in greater detail. With reference to FIG. 2A, the syringe 12 generally has a cylindrical syringe barrel 18 formed from glass, metal, or a suitable medical-grade plastic. The barrel 18 has a proximal end 20 and a distal end 24, with a sidewall 19 extending therebetween along a length of a longitudinal axis 15 extending through a center of the barrel 18. In some examples, the distal end 24 may have a conical shape that narrows in a distal direction from the cylindrical barrel 18. A nozzle 22 extends from the distal end 24. The barrel 18 has an outer surface 21 and an inner surface 23 (shown in FIG. 9) that defines an interior volume 25 configured for receiving the fluid therein. The proximal end 20 of the barrel 18 may be sealed with the plunger 26 (shown in FIG. 3) that is slidable through the barrel 18. The plunger 26 (shown in FIGS. 1 and 9) forms a liquid-tight seal against the inner surface 23 of the barrel 18 as it is advanced therethrough.

With continued reference to FIG. 2A, the proximal end 20 of the syringe 12 is sized and adapted for being removably inserted in the syringe port 16 of the injector 10 (shown in FIG. 1). In some examples, the proximal end 20 of the syringe 12 defines an insertion section 30 that is configured to be removably inserted into the syringe port 16 of the injector 10 while the remaining portion of the syringe 12 remains outside of the syringe port 16. As described in detail herein, in certain examples, the proximal end 20 of the syringe 12 includes one or more syringe retaining members 32 adapted to form a locking engagement with a corresponding locking mechanism in the syringe port 16 of the injector 10 for retaining the syringe 12 in the syringe port 16. The combination of the syringe 12 having the one or more syringe retaining members 32 and the locking mechanism of the injector 10 defines a connection interface for loading and unloading of the syringe 12 to and from the injector 10. In some examples, the one or more syringe retaining members 32 cooperate with at least a portion of the locking mechanism to self-orient the syringe 12 relative to the syringe port 16 such that the syringe 12 may be releasably locked with the syringe port 16.

The one or more syringe retaining members 32 may be provided on an outer surface 21 of the syringe barrel 18 on at least a portion of the insertion section 30. The one or more syringe retaining members 32 may be formed integrally with the barrel 18 or may be affixed or otherwise secured to the outer surface 21 of the barrel 18 using, for example, a frictional fit and/or an adhesive, welding, or by molding. In other examples, the one or more syringe retaining members 32 may be formed on the outer surface 21 of the barrel 18 by etching, laser cutting, or machining.

The one or more syringe retaining members 32 may be identical to or different from one another. In the example shown in FIG. 2A, the syringe 12 may have two sets of three different syringe retaining members 32. For example, the syringe 12 may have a pair of first syringe retaining members 32a positioned diametrically opposite to one another, a pair of second syringe retaining members 32b circumferentially offset relative to the pair of first syringe retaining members 32a in a first direction, and a pair of third syringe retaining members 32c circumferentially offset relative to the pair of first syringe retaining members in a second direction. The first, second, and third syringe retaining members 32a, 32b, 32c are collectively referred to as "syringe retaining members 32". With this arrangement, each first syringe retaining member 32a is surrounded by the second syringe retaining member 32b on one side thereof and the third syringe retaining member 32c on the other side thereof. One of ordinary skill in the art will appreciate that other arrangements of one or more sets of same or different syringe retaining members 32 can be easily conceived.

Figure 2B:
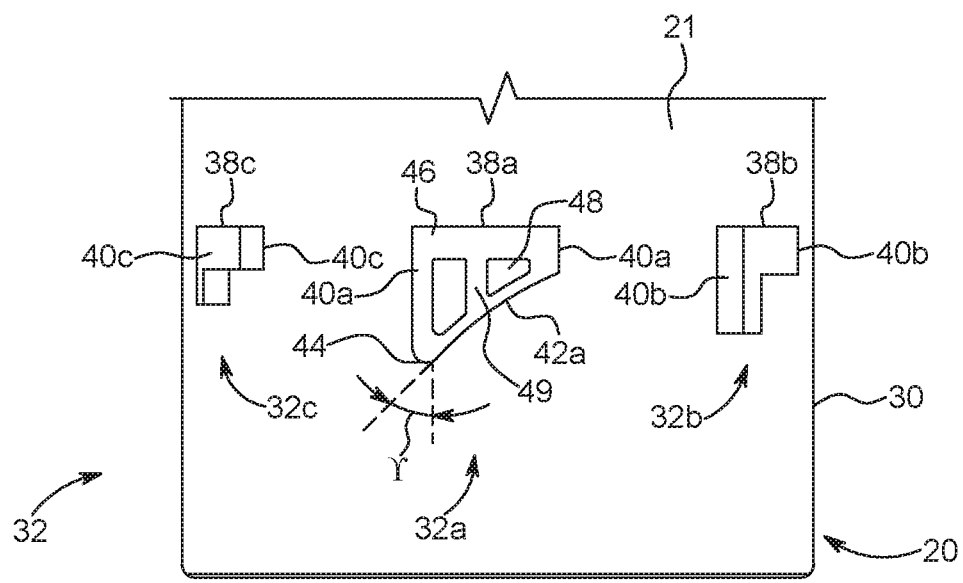
FIG. 2B is a detailed side view of at least one syringe retaining member of the syringe shown in FIG. 2A.

With reference to FIG. 2B, in examples where a plurality of first syringe retaining members 32a are provided, the first syringe retaining members 32a may be separated radially about the circumference of the barrel 18 by portions of the outer surface 21 of the barrel 18. In examples where two first syringe retaining members 32 are provided, the first syringe retaining members 32 may be diametrically opposed to one another (i.e., separated by 180° from each other). Each first syringe retaining member 32a may extend over an angle α (shown in FIG. 2A) along an outer circumference of the barrel 18. In some examples, angle α may be approximately 30°. In other examples, each first syringe retaining member 32a may extend at an angle which may be more than 30° or less than 30° of the outer circumference of the barrel 18. Similarly, each second and third syringe retaining member 32b, 32c may extend at the same or different angle as each first syringe retaining member 32a. The portions of the outer surface 21 of the barrel 18 between the first syringe retaining member 32a and adjacent second and third syringe retaining members 32b, 32c may extend at an angle β (shown in FIG. 2A), which may be more than approximately 30° or less than approximately 30° of the circumference of the barrel 18. The first, second, and third syringe retaining members 32a, 32b, 32c may be aligned longitudinally along the longitudinal axis 15 from the proximal end 20. For example, distal ends of the first, second, and third syringe retaining members 32a, 32b, 32c may be positioned at a same distance from the proximal end 20. In other examples, at least one of the first, second, and third syringe retaining members 32a, 32b, 32c may be offset longitudinally relative to the rest of the syringe retaining members in a direction toward the proximal end 20 or the distal end 24.

With reference to FIG. 2B, each first syringe retaining member 32a is formed as a substantially triangular element that protrudes radially outwardly from the outer surface 21 of the syringe barrel 18 relative to the longitudinal axis 15 (shown in FIG. 2A). Each first syringe retaining member 32a may protrude radially outwardly from the outer surface 21 of the barrel 18 in a direction substantially perpendicular to the outer surface 21. In some examples, at least one of the first syringe retaining members 32a or portions of at least one of the first syringe retaining members 32a may protrude radially outwardly from the outer surface 21 of the barrel 18 at an obtuse or acute angle relative to the outer surface 21 of the barrel 18. Each first syringe retaining member 32a has a base surface 38a that is substantially perpendicular to the longitudinal axis 15 of the barrel 18 in a radial cross-sectional plane. In other examples, the base surface 38a may be angled relative to the direction of the longitudinal axis 15 as it extends around the outer circumference of the barrel 18 in a radial cross-sectional plane. The base surface 38a may be planar, segmented, arcuate, curved, or a combination thereof. In some examples, the base surface 38a may have a plurality of individual sections that together define the base surface 38a. The plurality of individual sections of the base surface 38a may be planar, segmented, arcuate, curved, or a combination thereof.

With continued reference to FIG. 2B, a pair of side surfaces 40a extends from at least one end of the base surface 38a in a direction substantially parallel to the longitudinal axis 15. The side surfaces 40a may have equal or unequal lengths in a direction along the longitudinal axis 15. In some examples, at least one side surface 40a may be angled relative to the longitudinal axis 15. The side surfaces 40a may be angled in a same direction or opposite directions relative to the direction of the longitudinal axis 15. Each side surface 40a may be directly connected with the base surface 38a. In some examples, at least one side surface 40a may be disconnected from the base surface 38a. Each side surface 40a may be planar, segmented, arcuate, curved, or a combination thereof. In some examples, each side surface 40a may have a plurality of individual sections that together define the at least one side surface 40a. The plurality of individual sections of each side surface 40a may be planar, segmented, arcuate, curved, or a combination thereof.

With continued reference to FIG. 2B, a guide surface 42a extends between the pair of side surfaces 40a. The guide surface 42a may be angled relative to the longitudinal axis 15. The angled arrangement of the guide surface 42a relative to the longitudinal axis 15 may be defined as an angle of inclination of the guide surface 42a in a cylindrical plan projection view in a direction from the distal end 24 (shown in FIG. 2A) toward the proximal end 20. For example, the guide surface 42a may be angled at an angle γ relative to the longitudinal axis 15. The guide surface 42a may be directly connected with at least one of the side surfaces 40a. In some examples, the guide surface 42a may be disconnected from at least one of the side surfaces 40a. The guide surface 42a may terminate at a rounded or sharp apex 44. The guide surface 42a may be planar, segmented, arcuate, curved, or a combination thereof. In some examples, the guide surface 42a may have a plurality of individual sections that together define the guide surface 42a. The plurality of individual sections of the guide surface 42a may be planar, segmented, arcuate, curved, or a combination thereof.

The base surface 38a, the side surfaces 40a, and the guide surface 42a define a border or an outline of the first syringe retaining member 32a. In some examples, a top surface 46 of the first retaining member 32a may be shaped to correspond to the curvature of the syringe barrel 18. In other examples, the top surface 46 may be angled relative to the outer surface 21 of the syringe barrel 18 such that a first end of the top surface 46 is higher than a second end of the top surface 46 relative to the syringe barrel 18. The top surface 46 may have a recess 48 extending radially inward toward the outer surface 21 of the syringe barrel 18. According to certain embodiments, at least one reinforcement rib 49 may optionally extend across at least a portion of the recess 48. In some examples, the at least one reinforcement rib 49 extends between the base surface 38a and the guide surface 42a in a direction substantially parallel with the longitudinal axis 15. According to other embodiments, the first retaining member 32a may be sufficiently rigid to not require the at least one reinforcement rib 49.

With continued reference to FIG. 2B, the second and third syringe retaining members 32b, 32c are formed as substantially L-shaped elements that protrude radially outwardly from the outer surface 21 of the syringe barrel 18 relative to the longitudinal axis 15. At least one of the second and third syringe retaining members 32b, 32c may protrude radially outwardly from the outer surface 21 of the barrel 18 in a direction substantially perpendicular to the outer surface 21. In some examples, at least one of the second and third syringe retaining members 32b, 32c or portions of at least one of the second and third syringe retaining members 32b, 32c may protrude radially outwardly from the outer surface 21 of the barrel 18 at an obtuse or acute angle relative to the outer surface 21 of the barrel 18.

Each of the second and third syringe retaining members 32b, 32c has a base surface 38b, 38c that is substantially perpendicular to the longitudinal axis 15 of the barrel 18. In other examples, the base surface 38b, 38c may be angled relative to the direction of the longitudinal axis 15 as it extends around the outer circumference of the barrel 18 in a radial cross-sectional plane. The base surface 38b, 38c may be planar, segmented, arcuate, curved, or a combination thereof. In some examples, the base surface 38b, 38c may have a plurality of individual sections that together define the base surface 38b, 38c. The plurality of individual sections of the base surface 38b, 38c may be planar, segmented, arcuate, curved, or a combination thereof. In some examples, the base surface 38b of the second syringe retaining member 32b may have the same length as the base surface 38c of the third syringe retaining member 32c. In other examples, the base surface 38b of the second syringe retaining member 32b may be longer or shorter than the base surface 38c of the third syringe retaining member 32c. At least one edge of the base surface 38b, 38c of the second and third syringe retaining members 32b, 32c may protrude from the outer surface 18 of the syringe barrel 18 at an obtuse or acute angle relative to the outer surface 21.

With continued reference to FIG. 2B, each of the second and third syringe retaining members 32b, 32c has a side surface 40b, 40c that extends from one end of the base surface 38b, 38c in a direction substantially parallel to the longitudinal axis 15. The side surfaces 40b, 40c may have equal or unequal length in a direction along the longitudinal axis 15. In some examples, at least one side surface 40b, 40c may be angled relative to the longitudinal axis 15. Each side surface 40b, 40c may be directly connected with the respective base surface 38b, 38c. In some examples, at least one side surface 40b, 40c may be disconnected from the respective base surface 38b, 38c. Each side surface 40b, 40c may be planar, segmented, arcuate, curved, or a combination thereof. In some examples, each side surface 40b, 40c may have a plurality of individual sections that together define the at least one side surface 40b, 40c. The plurality of individual sections of each side surface 40b, 40c may be planar, segmented, arcuate, curved, or a combination thereof. In some examples, the side surface 40b of the second syringe retaining member 32b may have the same length as the side surface 40c of the third syringe retaining member 32c. In other examples, the side surface 40b of the second syringe retaining member 32b may be longer or shorter than the side surface 40c of the third syringe retaining member 32c. At least one edge of the side surface 40b, 40c of the second and third syringe retaining members 32b, 32c may protrude from the outer surface 21 of the syringe barrel 18 at an obtuse or acute angle relative to the outer surface 21.

While FIGS. 2A-2B illustrate one non-limiting example of the one or more syringe retaining members 32, various other shapes are also contemplated. For example, the one or more syringe retaining members 32 may have a generally circular, square, rectangular, or any other polygonal shape. Various features may be provided on the one or more syringe retaining members 32 to help orient the syringe 12 relative to the syringe port 16 or to lock the syringe 12 with the syringe port 16. In each example, the one or more syringe retaining members 32 is configured for forming a locking engagement with a corresponding locking mechanism in the syringe port 16 of the injector 10 for retaining the syringe 12 in the syringe port 16.

With reference to FIG. 2A, drip flange 36 may extend radially outward from the outer surface 21 of the syringe barrel 18 relative to the longitudinal axis 15. The drip flange 36 may extend around at least a portion of the outer circumference of the barrel 18. In one example, the drip flange 36 is positioned distally along the longitudinal axis 15 relative to the syringe retaining member 32. The drip flange 36 may be configured to prevent fluid that drips from the nozzle 22 from entering the syringe port 16 on the injector 10. In this manner, the drip flange 36 helps reduce the amount of fluid that may enter the syringe port 16 and jam or interfere with the connection interface 100. In some examples, the drip flange 36 defines a stop surface that delimits the insertion section 30 of the syringe 12, such as when the drip flange 36 contacts a top surface of the cover 72 (shown in FIG. 9). The drip flange 36 may be formed integrally with the barrel 18 or it may be affixed or otherwise secured to the outer surface 21 of the barrel 18 using, for example, a frictional fit and/or an adhesive, welding, or by molding. In other examples, the drip flange 36 may be formed on the outer surface 21 of the barrel 18 by etching, laser cutting, or machining.

Figure 3:
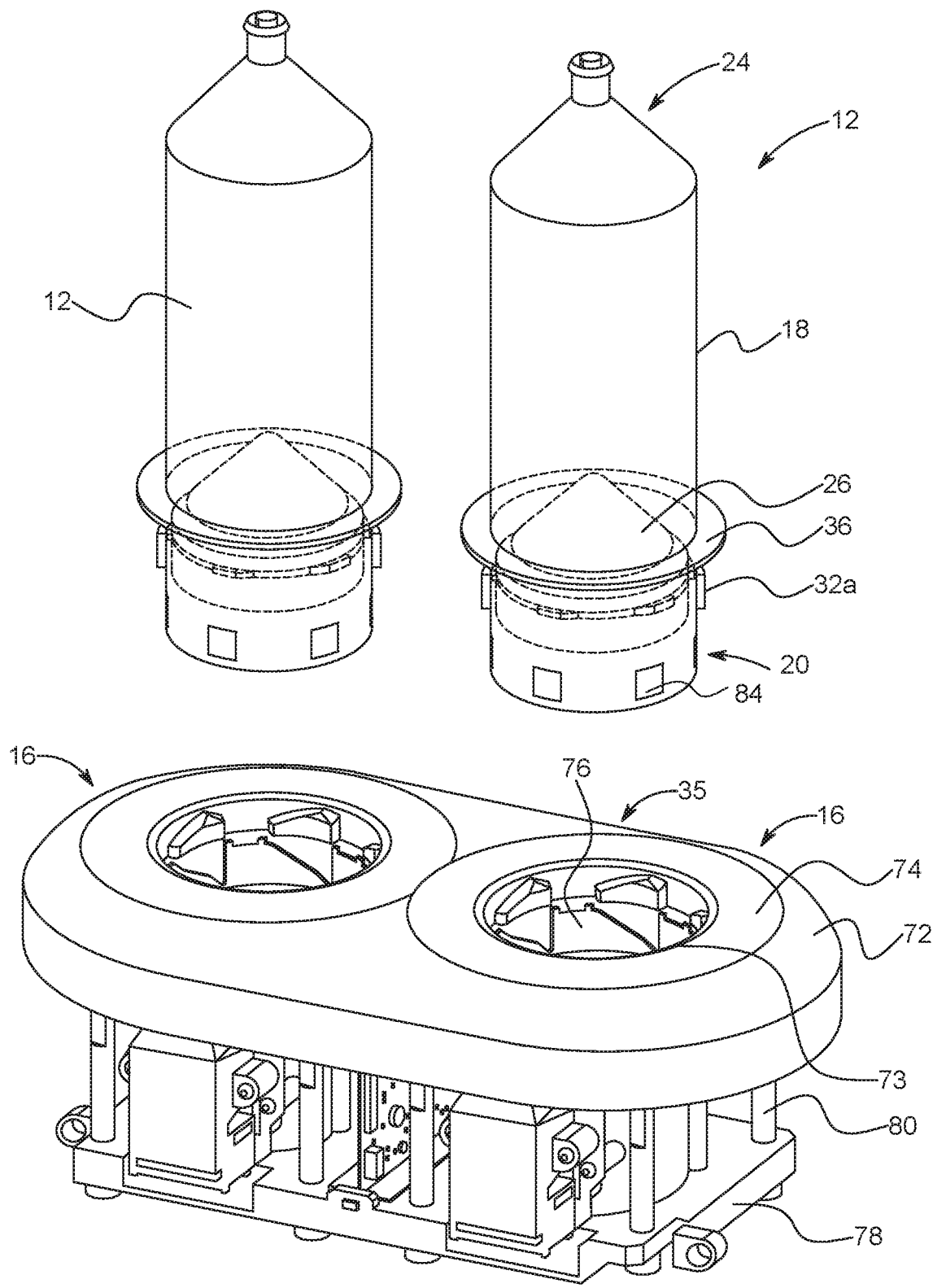
FIG. 3 is an exploded perspective view of two syringes and a dual locking mechanism for securing one or both syringes to a fluid injector according to one example.

With reference to FIG. 3, the proximal end 20 of each syringe 12 is sized and adapted for being removably inserted in the syringe ports 16 of the injector 10 (shown in FIG. 1). Each syringe port 16 has a locking mechanism 35 configured to operatively engage the one or more syringe retaining members 32 of the syringe 12. The one or more syringe retaining members 32 may be operatively engaged with the locking mechanism 35 between a locked position, wherein the syringe 12 is locked in the syringe port 16 and cannot be removed therefrom, and an unlocked position, wherein the syringe 12 is unlocked from the syringe port 16 and can be freely removed from the syringe port 16 or inserted into the syringe port 16.

Figure 4:
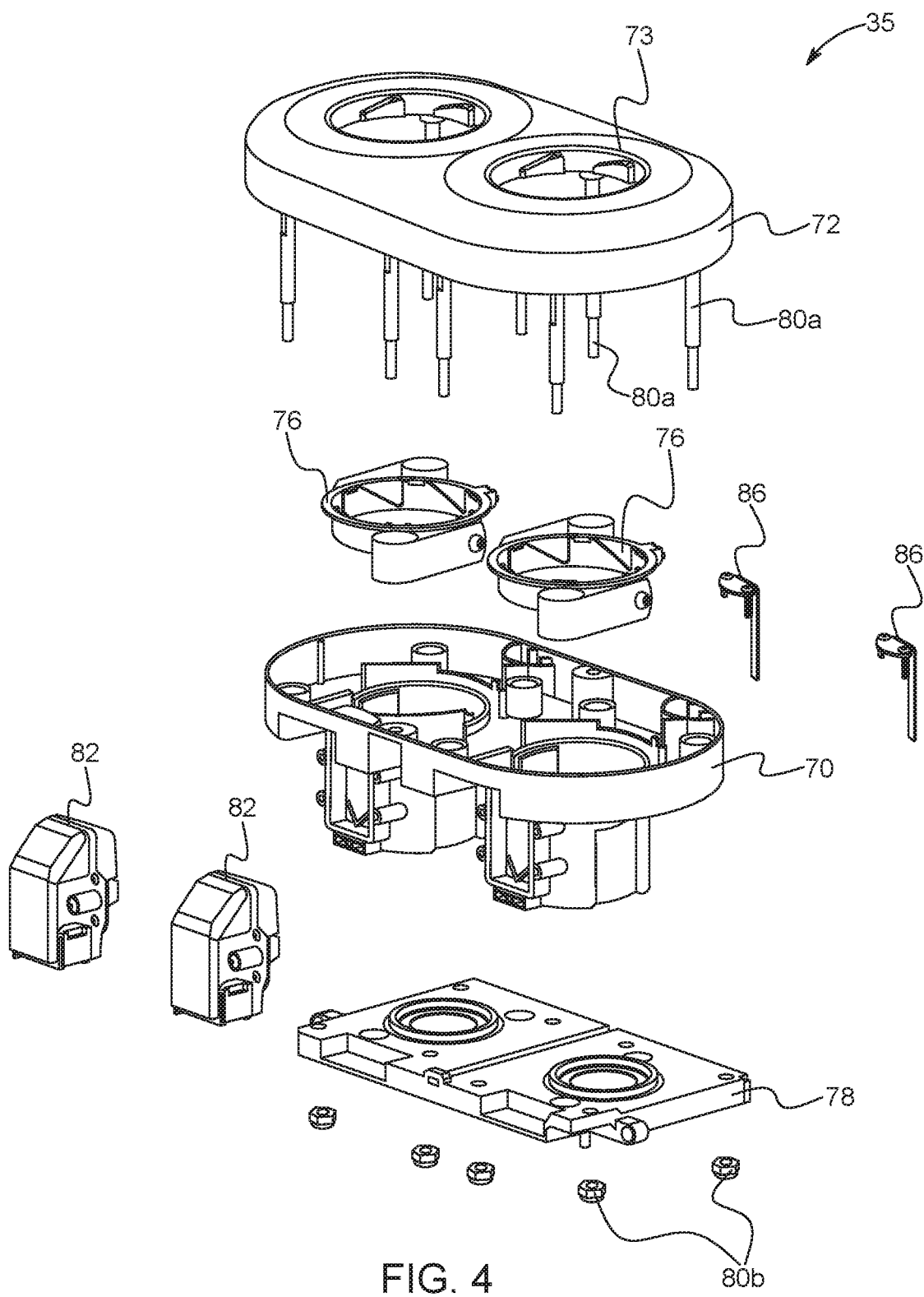
FIG. 4 is an exploded perspective view of the locking mechanism shown in FIG. 3.

With reference to FIG. 4, and with continued reference to FIG. 3, the locking mechanism 35 has a housing 70 and a removable cover plate 72 attached to the housing 70. The cover plate 72 has a pair of central openings 73 each configured to receive the proximal end 20 of the syringe 12. In some examples, the cover plate 72 may have a single central opening 73 for receiving a single syringe 12. The cover plate 72 may have indicia 74 thereon for identifying the syringe that should be connected to the syringe port 16. For example, the indicia 74 may indicate the type of syringe 12 that should be connected to the syringe port 16 based on the fluid (i.e., saline or contrast) in the syringe 12. The housing 70 and the cover plate 72 of the locking mechanism 35 may be integrated as part of the housing 14 of the injector 10 (shown in FIG. 1).

With continued reference to FIGS. 3-4, each syringe port 16 has a locking ring 76 configured to operatively engage the one or more syringe retaining members 32 of the syringe 12. The locking ring 76 is coaxial with the opening 73 of the syringe port 16 such that the syringe 12 inserted through the opening 73 is also inserted through the locking ring 76. A diameter of the locking ring 76 may be substantially identical to a diameter of the opening 73. The locking ring 76 may be movable between a first position, wherein the syringe 12 can be inserted into the syringe port 16 prior to locking with the locking mechanism 35 or removed from the syringe port 16 following unlocking from the locking mechanism 35, and a second position, wherein the syringe 12 is locked with the locking mechanism 35. A sensor 86 (shown in FIG. 4) may be provided for detecting a position of the locking ring 76, such as an angular position of the locking ring 76 between the first position and the second position. The housing 70 may be connected to a base plate 78 using, for example, a plurality of fasteners 80. In some examples, the plurality of fasteners 80 may include a plurality of bolts 80a connected to an underside portion of the cover plate 72 and a plurality of nuts 80b threadably attached to the bolts 80a. Each of the bolts 80a extends through openings on the housing 70 and the base plate 78. In some examples, the bolts 80a may be threadably connected with at least one of the housing 70 and the base plate 78.

With reference to FIG. 4, at least one syringe port 16 may have a barcode reader system 82 configured for reading at least one identification tag 84 on the syringe 12 (shown in FIG. 3) having identifying information about at least one property of the syringe 12 and/or the fluid contained therein. In some examples, information that can be stored in the at least one identification tag 84 includes, without limitation, information regarding production data of the syringe, such as the date and time of manufacture, lot number, production line, plant code, and/or shelf life. In other examples, information that can be stored in the at least one identification tag 84 includes, without limitation, information regarding the type of fluid stored in the syringe, volume of fluid, and/or shelf life. In other examples, information that can be stored in the at least one identification tag 84 includes, without limitation, information regarding a unique digital signature that can be verified by the fluid injector 10 to confirm that an authentic syringe 12 is used with the fluid injector 10. Any and all of this information may be stored in each of the at least one identification tag 84.

Figure 5:
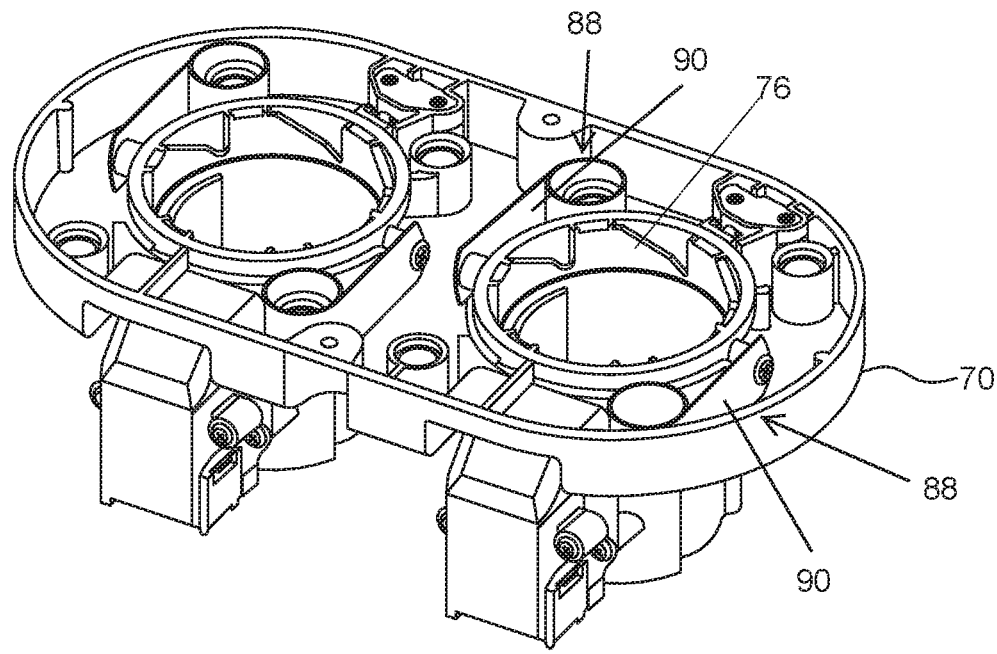
FIG. 5 is a top perspective view of the locking mechanism shown in FIG. 3 without a front cover.

With reference to FIG. 5, movement of the locking ring 76 between the first position and the second position may be controlled by at least one biasing mechanism 88 ("biasing mechanism 88"). In some examples, the biasing mechanism 88 may be configured to bias the locking ring 76 to the first position such that when the locking ring 76 is moved from the first position, the biasing mechanism 88 automatically urges the locking ring 76 back toward the first position. In some examples, the biasing mechanism 88 may be at least one spring 90. In other examples, the biasing mechanism 88 may be a pair of springs 90. The springs 90 may be positioned diametrically opposite to one another. The at least one spring 90 may be a constant force spring having a first end attached to the locking ring 76 and a second end attached to the housing 70. Movement of the locking ring 76 from a first position toward a second position, such as by rotation about its central axis, generates a restoring force in the at least one spring 90. Upon release of an urging force that moves the locking ring 76 from the first position to the second position, the restoring force of the at least one spring 90 automatically urges the locking ring 76 back toward the first position. In some examples, the housing 70 may have one or more stops 92 for delimiting a range of angular movement of the locking ring 76 between the first position and the second position. Each of the one or more stops 92 may be configured for engaging a tab 94 on the locking ring 76.

Figure 6:
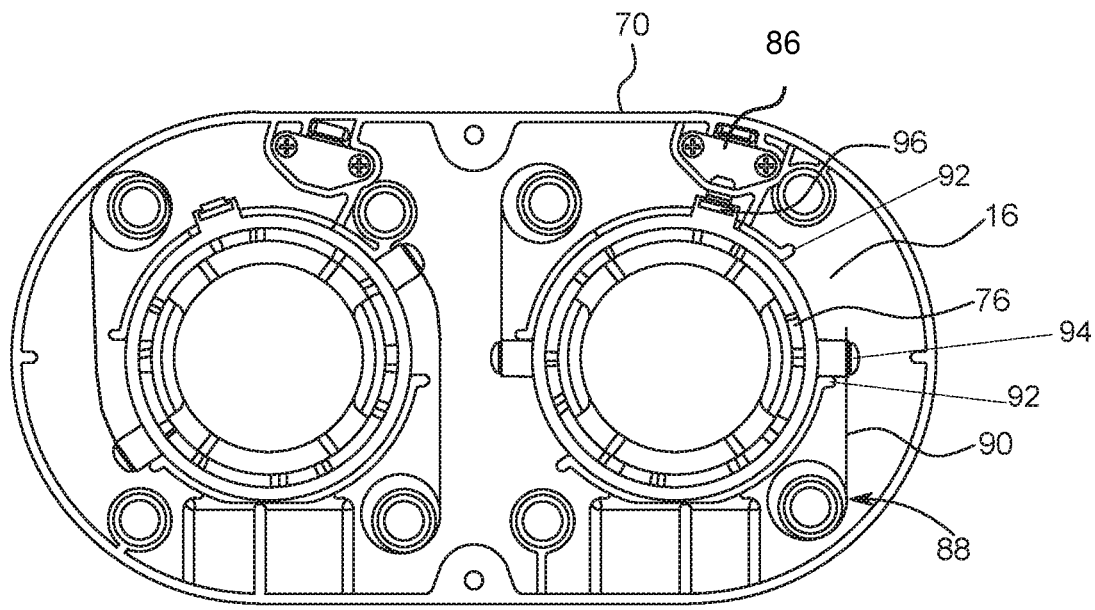
FIG. 6 is a top view of the locking mechanism shown in FIG. 5 with a left locking ring shown in a second position and a right locking ring shown in a first position.

With reference to FIG. 6, each syringe port 16 has the sensor 86 configured for detecting a position of the locking ring 76, such as an angular position of the locking ring 76 between the first position and the second position. Each locking ring 76 may have a sensor pickup 96 configured for interacting with the sensor 86. In some examples, the sensor pickup 96 may be a magnet. The sensor 86 may vary its output voltage based on the strength of the magnetic field of the sensor pickup 96. In this manner, the sensor 86 and the sensor pickup 96 operate as a Hall effect sensor. The sensor 86 may be a binary sensor configured to detect a presence or absence of the sensor pickup 96. In such examples, the sensor 86 can only determine whether the locking ring 76 is at a particular orientation, such as whether the locking ring 76 is in a first position or the second position. The sensor 81 sensor 86 may be a digital sensor configured to detect a position of the sensor pickup 96, and therefore the position of the locking ring 76, relative to the sensor 86. In further examples, the sensor 86 may be an analog sensor, such as a non-binary analog sensor, configured to provide a range of voltage outputs based on whether the locking ring 76 is in a locked position, an unlocked position, or a position between the locked position and the unlocked position. In some examples, the sensor 86 may be an optical sensor, such as a camera, configured for detecting a position of the sensor pickup 96. One of ordinary skill in the art will appreciate that the sensor 86 may be any type of sensor that is configurable for detecting a position of the locking ring 76 relative to the sensor 86.

Figure 7A:
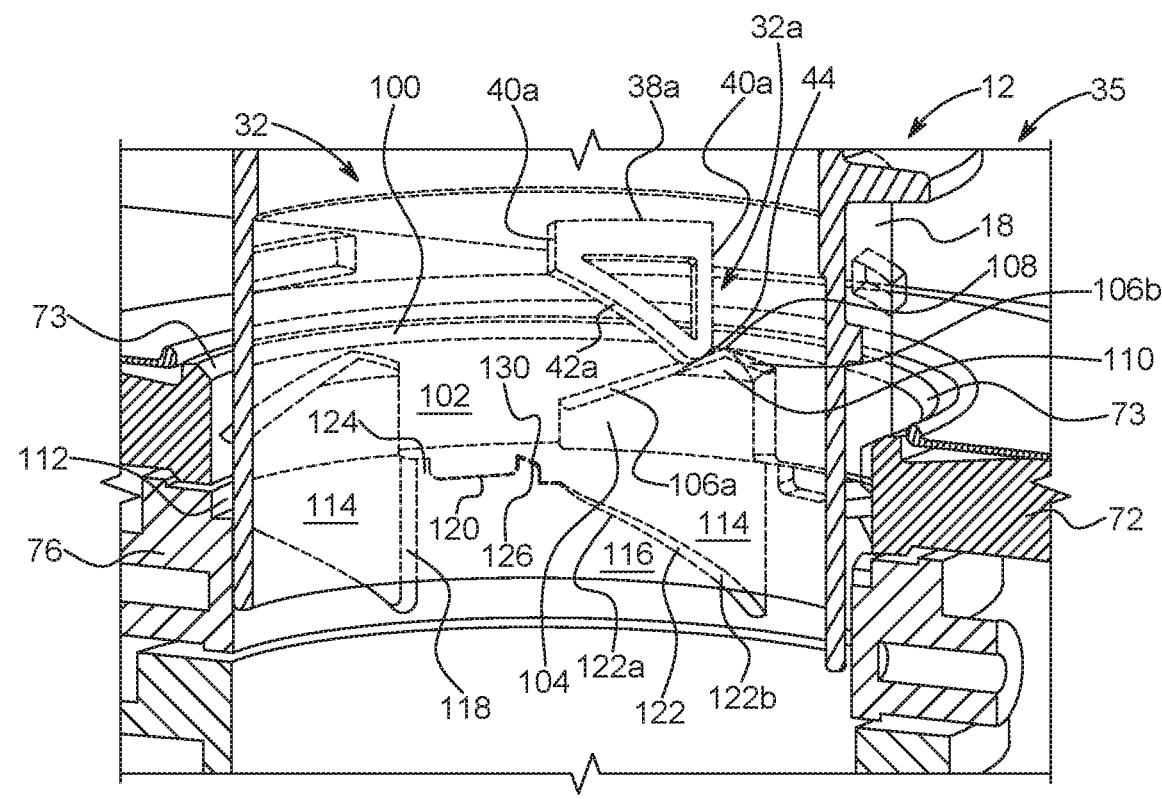
FIGS. 7A-7H are partially-transparent perspective views of the locking mechanism and the syringe showing movement of components of the locking mechanism during engagement of the syringe with the locking mechanism.
Figure 7B:
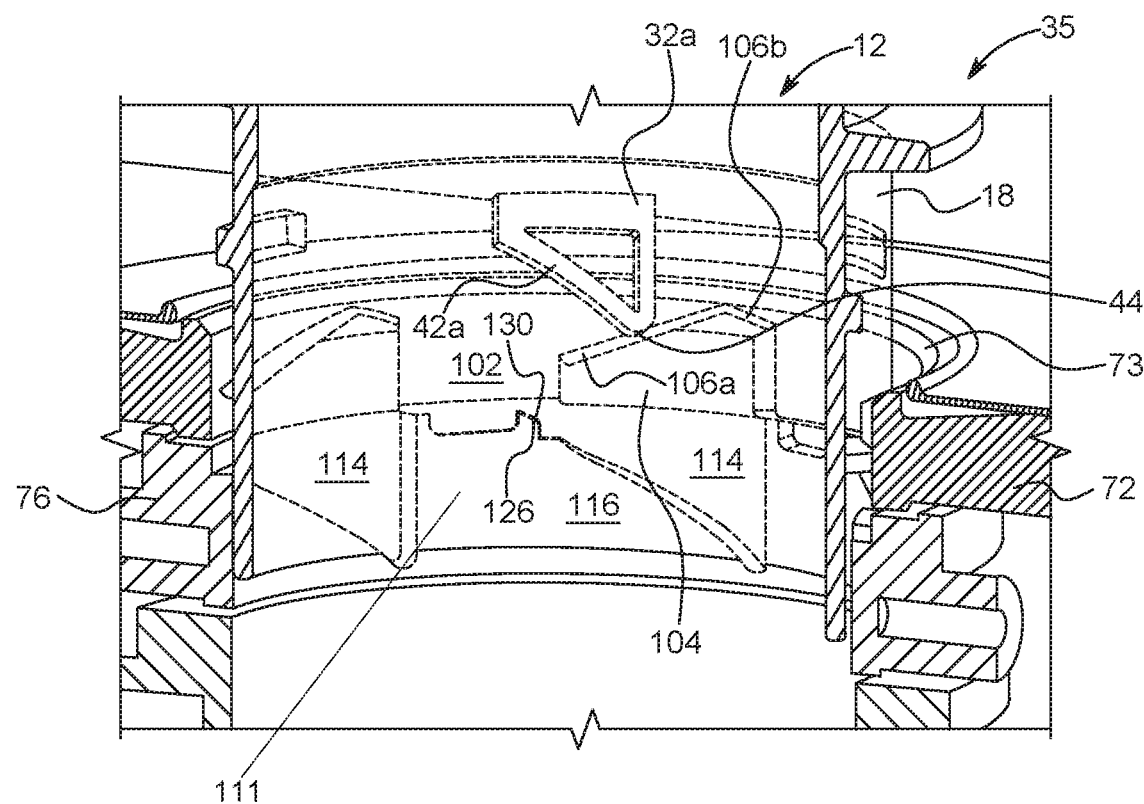

With reference to FIG. 7A, an inner portion of a sidewall 100 within the opening 73 of the cover plate 72 has one or more first recesses 102 that are configured to receive the syringe retaining members 32 of the syringe 12 when the insertion section 30 of the syringe 12 is inserted through the opening 73 of the cover plate 72. Each first recess 102 extends substantially parallel along a direction of the longitudinal axis of the opening 73. The one or more first recesses 102 are spaced about the inner circumference of the sidewall 100 at intervals that correspond to the spacing of the syringe retaining members 32 about the outer circumference of the syringe 12. A width of each first recess 102 is the same or larger than a width of the syringe retaining members 32. The first recesses 102 define a clearance space for receiving the syringe retaining member 32 on the syringe 12. The number of syringe retaining members 32 on the syringe 12 desirably corresponds to the number of the first recesses 102 on the sidewall 100 of the cover plate 72. In other examples, the number of syringe retaining members 32 on the syringe 12 may be smaller than the number of the first recesses 102 on the sidewall 100 of the cover plate 72. In such examples, the syringe retaining members 32 on the syringe 12 may be spaced apart along an outer circumference of the syringe barrel 18 such that each syringe retaining member 32 can be aligned with a corresponding first recess 102 on the cover plate 72. In other examples, the number of syringe retaining members 32 on the syringe 12 may be higher than the number of first recesses 102 on the sidewall 100 of the cover plate 72 such that more than one syringe retaining member 32 may be received within at least one first recess 102.

The sidewall 100 of the opening 73 between the recesses 102 is configured for guiding the syringe retaining members 32 toward the locking ring 76 into self-orienting alignment with the syringe port 16 during insertion of the syringe 12 into the syringe port 16. The sidewall 100 has at least one or a plurality of first guide members 104 arranged such that a first guide member 104 is positioned between each pair of recesses 102. A width of each first guide member 104 may be equal to or smaller than a width of the sidewall of the syringe barrel 18 between adjacent syringe retaining members 32. Each first guide member 104 has one or more guiding surfaces for guiding the syringe retaining members 32 toward the locking ring 76 during insertion of the syringe 12 into the syringe port 16. In this manner, the first guide member 104 guides the syringe 12 into self-orienting alignment with the locking ring 76. In some examples, each first guide member 104 may have one or more guiding ramps 106a, 106b that are inclined or angled toward the first recesses 102 on either side of the first guide member 104. For example, as shown in FIG. 7A, a first guiding ramp 106a may extend in a first direction from an apex 108 of the first guide member 104 toward a first recess 102 on one side of the first guide member 104 and a second guiding ramp 106b may extend in a second direction from the apex 108 toward a first recess 102 on the other side of the first guide member 104. The syringe retaining member 32, such as the first syringe retaining member 32a, is configured to engage one of the first guiding ramp 106a or the second guiding ramp 106b with the apex 44 and/or the guide surface 42a if the syringe 12 is oriented such that the syringe retaining members 32 are not aligned with the recesses 102. The apex 44 and/or the guide surface 42a of the first syringe retaining member 32a is configured to move along the first guiding ramp 106a or the second guiding ramp 106b, which causes the syringe barrel 18 to rotate about the longitudinal axis 15. In this manner, the syringe retaining members 32 which are initially misaligned relative to the corresponding one or more first recesses 102, such as due to angular misalignment in a direction about the longitudinal axis 15, are brought in alignment with the one or more first recesses 102 by the one or more guiding ramps 106a, 106b such that the syringe retaining members 32 can be inserted into the first recesses 102.

The first and second guiding ramps 106a, 106b may have an equal or unequal angle of inclination relative to the apex 108. In specific embodiments having unequal angles, the angles may be of a ratio that increase the probability that the syringe will be rotated in a particular direction (i.e., clockwise or counterclockwise) when it is inserted into the first recess 102. Additionally, the first and second guiding ramps 106a, 106b may have the same or different lengths. In some examples, the first guide members 104 may have a chamfer 110 at the apex 108 that is configured to guide the syringe 12 into the opening 73 such that the longitudinal axis 15 of the syringe barrel 18 is coaxial with the longitudinal axis of the opening 73.

With continued reference to FIG. 7A, the locking mechanism 35 further includes the locking ring 76 having a substantially annular shape with an inner sidewall 111. The locking ring 76 is coaxial with the opening 73 of the cover plate 72 and is positioned proximally of the cover plate 72. As discussed herein, the locking ring 76 is rotationally movable about its longitudinal axis and axially fixed relative to the cover plate 72 and the housing 70. The locking ring 76 may be biased in a particular orientation by the biasing mechanism 88 (shown in FIG. 5). The locking ring 76 has a plurality of second recesses 114. Each second recess 114 is configured to receive the one or more of the syringe retaining members 32 of the syringe 12 when the insertion section 30 of the syringe 12 is inserted into and locked within the locking mechanism 35. The one or more second recesses 114 are arranged around a circumference of the inner sidewall 111 of the locking ring 76 and extend radially into the inner sidewall 111. Adjacent second recesses 114 are separated from each other by a second guide member 116. The locking ring 76 may have an equal or unequal number of second recesses 114 to the number of second guide members 116. In a first position of the locking ring 76, such as when the syringe 12 is not present, the second recesses 114 are positioned directly below the first guide member 104. In this same position of the locking ring 76, a first portion of the second guide member 116 is positioned directly below the first recess 102, while a second portion of the second guide member 116 is positioned directly below the first guide member 104.

With continued reference to FIG. 7A, the second guide member 116 has a stop surface 118, a top surface 120, and a ramp surface 122. The stop surface 118 is configured for engaging the side surfaces 40a, 40b, 40c of the syringe retaining members 32 when the syringe retaining members 32 are positioned within the second recesses 114. The stop surface 118 of the second guide member 116 prevents rotation of the syringe 12 relative to the locking mechanism 35 when the syringe 12 is locked within the locking mechanism. The stop surface 118 may be substantially parallel with the longitudinal axis 15 of the syringe 12 when the syringe 12 is engaged with the locking mechanism 12. In some examples, the stop surface 118 may be angled relative to the longitudinal axis 15 of the syringe 12. In further examples, the stop surface 118 may be connected to or disconnected from the top surface 120. The stop surface 118 may be planar, segmented, arcuate, curved, or a combination thereof. In some examples, the stop surface 118 may have a plurality of individual sections that together define the stop surface 118. The plurality of individual sections of the stop surface 118 may be planar, segmented, arcuate, curved, or a combination thereof.

With continued reference to FIG. 7A, the top surface 120 may be substantially perpendicular to the longitudinal axis 15 of the syringe 12 when the syringe 12 is engaged with the locking mechanism 35. The top surface 120 of the second guide member 116 is positioned at the bottom of the first recess 102 to prevent access to the second recesses 114 until movement of the syringe 12 in the proximal direction causes a rotation of the locking ring 76, as described herein. The top surface 120 may be spaced apart in a proximal direction form a bottom edge of the first guide member 104. The top surface 120 may have one or more safety catches 124, 126. In some examples, a first safety catch 124 may be positioned at an end of the top surface 120 that connects with the stop surface 118. The first safety catch 124 prevents insertion of any portion of the syringe 12 or other object into a space between the bottom surface of the first guide member 104 and the top surface 120 of the second guide member 116. A second safety catch 126 may be positioned at an end of the top surface 120 that connects with the ramp surface 122. In some examples, the second safety catch 126 may be offset from a transition point between the top surface 120 and the ramp surface 122 such that the second safety catch 126 is positioned between the first safety catch 124 and the transition point between the top surface 120 and the ramp surface 122. The second safety catch 126 may have a sloped portion 130 that is angled in a direction toward the ramp surface 122. In this manner, when the syringe retaining member 32, such as the apex 44 and/or the guide surface 42a of the first syringe retaining member 32, contacts the second safety catch 126, the sloped portion 130 of the second safety catch 126 guides the apex 44 and/or the guide surface 42a toward the ramp surface 122. In some examples, the top surface 120 may be connected to or disconnected from the stop surface 118 and/or the ramp surface 122. The top surface 120 may be planar, segmented, arcuate, curved, or a combination thereof. In some examples, the top surface 120 may have a plurality of individual sections that together define the top surface 120. The plurality of individual sections of the top surface 120 may be planar, segmented, arcuate, curved, or a combination thereof.

With continued reference to FIG. 7A, the ramp surface 122 may be connected to or disconnected from the top surface 120. A proximal end of the ramp surface 122 of one second guide member 116 connects with the stop surface 118 of an adjacent second guide member 116 The ramp surface 122 may be planar, segmented, arcuate, curved, or a combination thereof. In some examples, the ramp surface 122 may have a plurality of individual sections 122a, 122b that together define the ramp surface 122. The individual sections 122a, 122b of the ramp surface 122 may have a different length and/or slope relative to one another. The individual sections 122a, 122b of the ramp surface 122 may be planar, segmented, arcuate, curved, or a combination thereof.

Having described the structure of the syringe 12, the syringe retaining members 32, and the locking mechanism 35, a method of inserting and removing the syringe 12 into the syringe port 16 to lock or unlock the syringe 12 with the locking mechanism 35 will now be described with reference to FIGS. 7A-8D. FIGS. 7A-7H show a sequence of movements of the syringe 12 and the locking ring 76 of the locking mechanism 35 during insertion of the syringe 12 into the syringe port 16 to lock the syringe 12 using the locking mechanism 35. FIGS. 8A-8D show a sequence of movements of the syringe 12 and the locking ring 76 of the locking mechanism 35 during removal of the syringe 12 from the syringe port 16 to unlock the syringe 12 from the locking mechanism 35. While the following discussion focuses on movement of a single first syringe retaining member 32a relative to first and second guide members 104, 116 of the locking mechanism 35, it is to be understood that the remaining syringe retaining members 32 move in a corresponding manner.

Figure 7C:
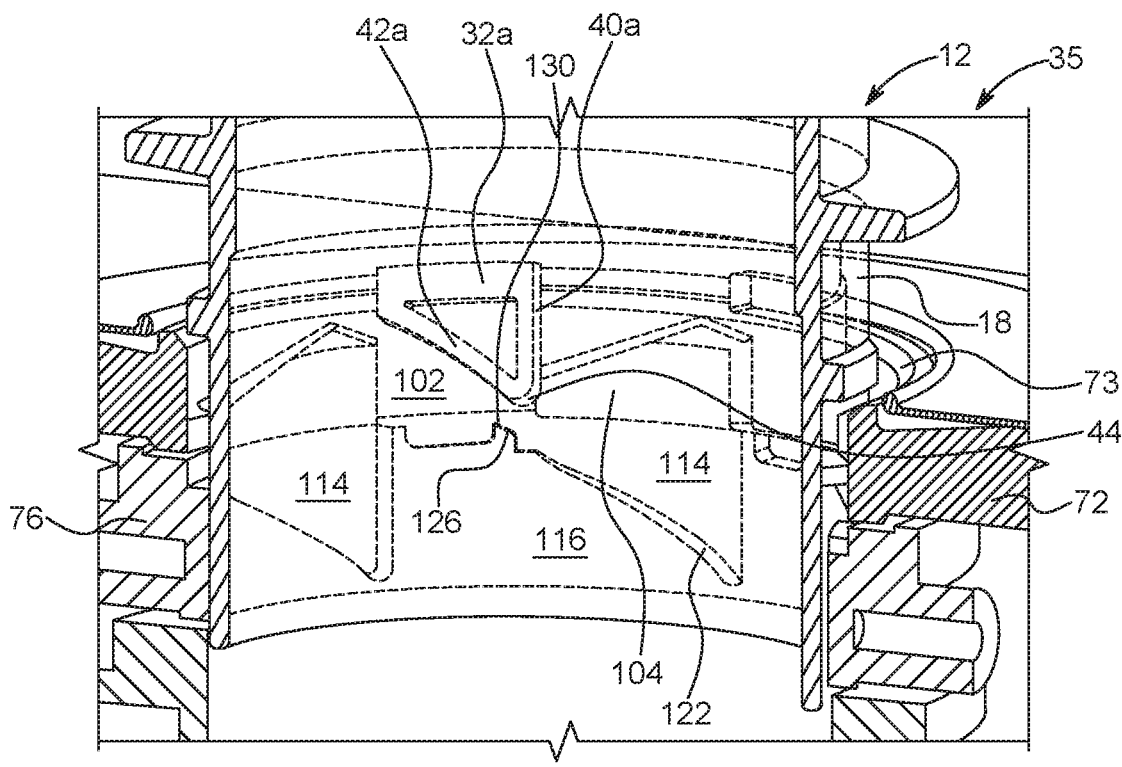

To insert the syringe 12 into the syringe port 16, the insertion section 30 of the syringe 12 is inserted into the opening 73 defining the syringe port 16 on the cover plate 72. The chamfer 110 of the first guide members 104 self-aligns the longitudinal axis 15 of the syringe barrel 18 with the longitudinal axis of the opening 73. In this manner, the syringe 12 can be brought into coaxial alignment with the opening 73 and, therefore, the locking mechanism 35. If the first syringe retaining members 32a on the syringe 12 are initially misaligned relative to the first recesses 102 on the cover plate 72 (i.e., first syringe retaining members 32a are not aligned for insertion into the first recesses 102), the guiding ramps 106a, 106b of the each first guide member 104 rotationally guide the syringe 12 into self-orienting alignment with the first recesses 102 due to sliding of the first syringe retaining member 32a along the first or second guiding ramps 106a, 106b (FIG. 7A). The apex 44 and/or the guide surface 42a of the first syringe retaining member 32a is guided along the first or second guiding ramp 106a, 106b (FIG. 7B) until the apex 44 reaches the end of the first or second guiding ramp 106a, 106b and the first syringe retaining member 32a is aligned with the first recess 102 such that the first syringe retaining member 32a can drop into the first recess 102 (FIG. 7C). The sloped portion 130 of the second safety catch 126 may guide the apex 44 and/or the guide surface 42a of the first syringe retaining member 32a toward the ramp surface 122. At this stage, the syringe 12 has self-aligned with the locking mechanism 35, but the syringe is not locked with the locking mechanism 35 and can be removed freely by withdrawing the first syringe retaining member 32a from the first recess 102.

Figure 7D:
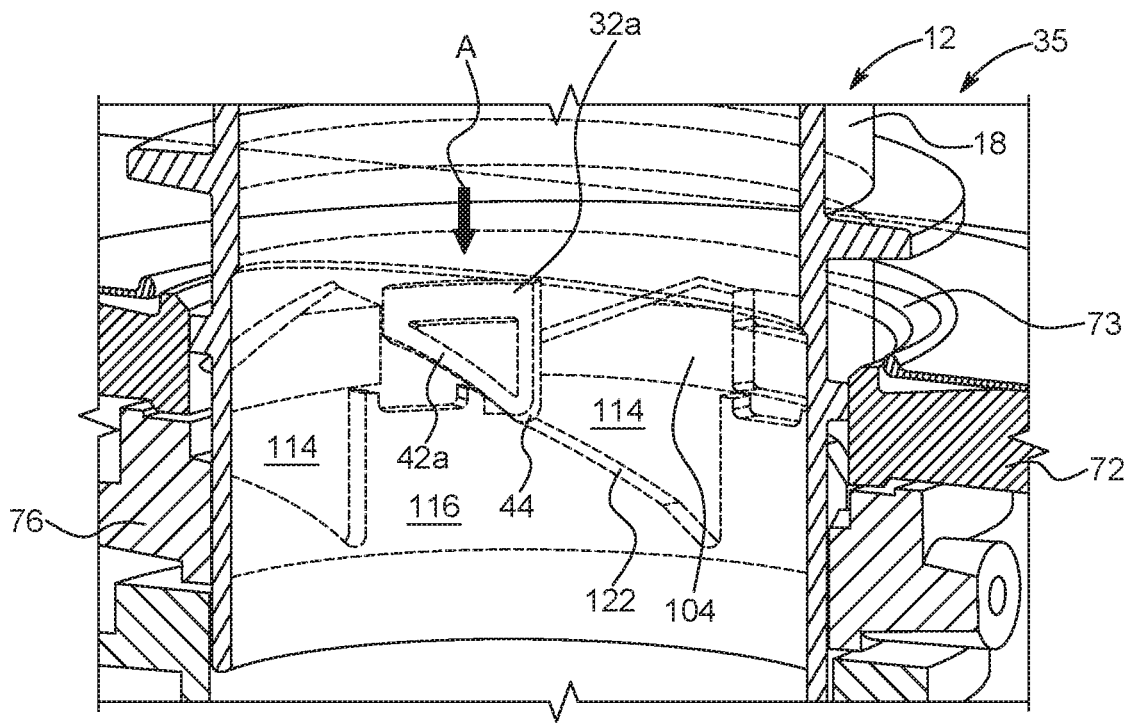
Figure 7E:
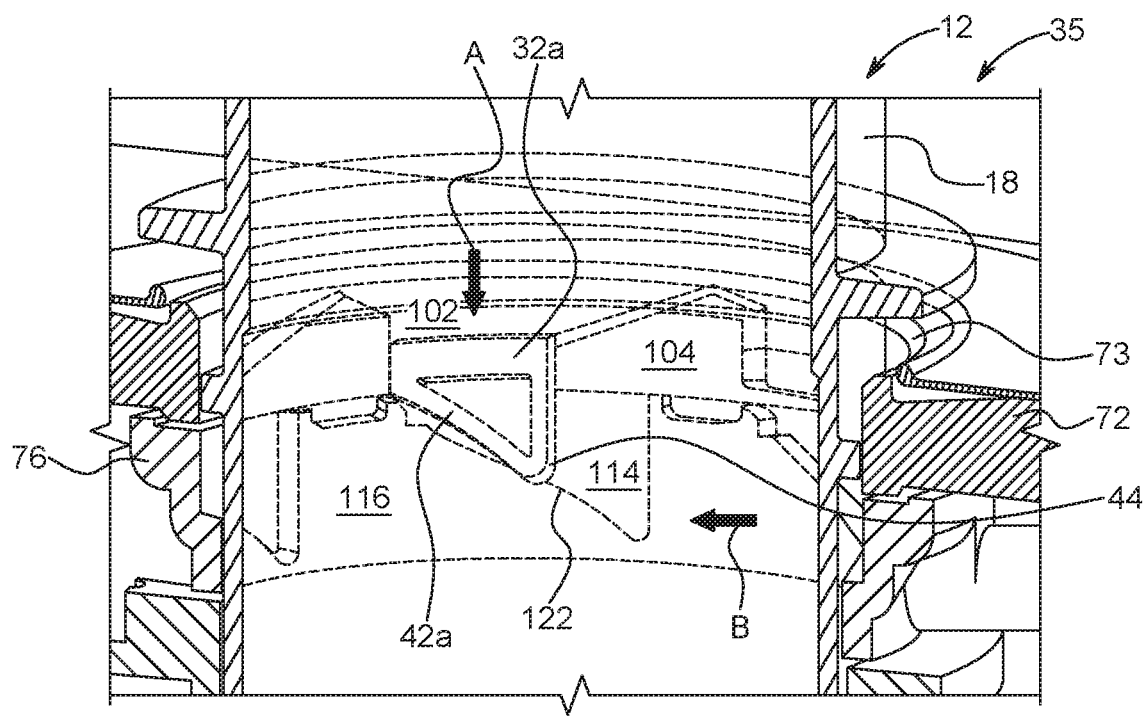

With reference to FIG. 7D, to lock the syringe 12 with the locking mechanism 35, the syringe 12 is moved proximally in a direction of arrow A toward the locking ring 76. Proximal movement of the syringe 12 relative the locking ring 76 causes the apex 44 and/or the guide surface 42a of the first syringe retaining member 32 to contact the ramp surface 122 of the locking ring 76. Because the locking ring 76 cannot move axially in the direction of movement of the syringe 12, the locking ring 76 rotates about its longitudinal axis due to a normal force component between the apex 44 and/or the guide surface 42a of the first syringe retaining member 32a and the ramp surface 122 of the locking ring 76. This normal force acts against the biasing force of the biasing mechanism 88 (shown in FIG. 5) and causes the locking ring 76 to rotate in a direction of arrow B shown in FIG. 7E.

Figure 7F:
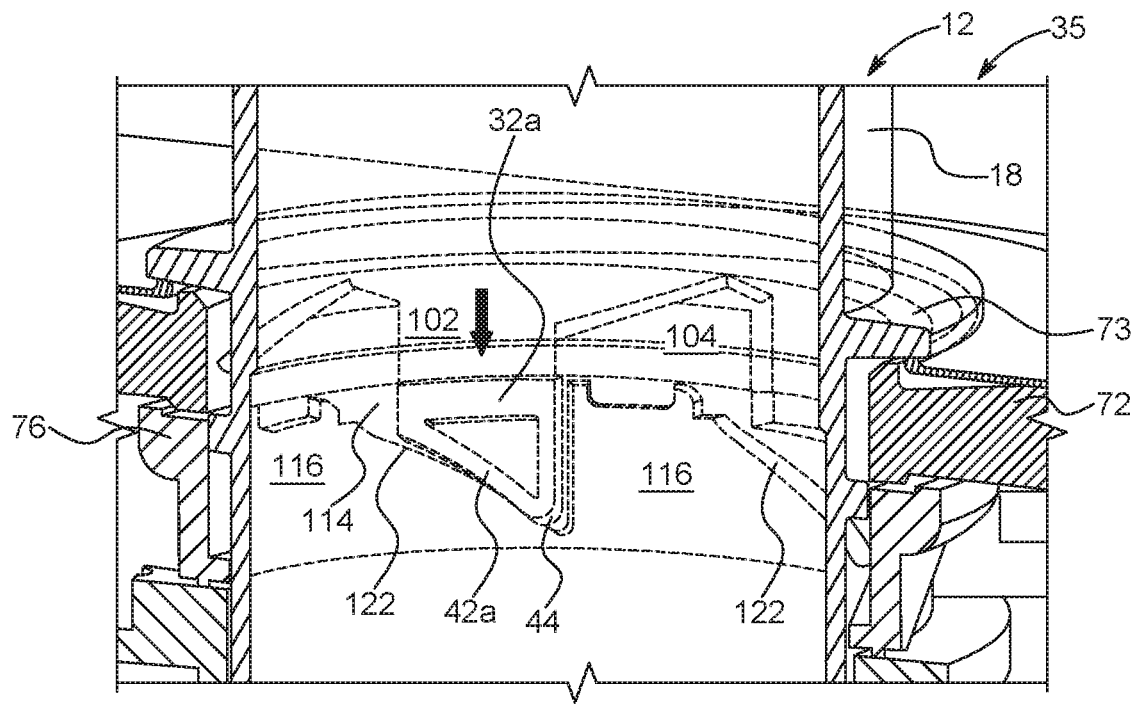
Figure 7G:
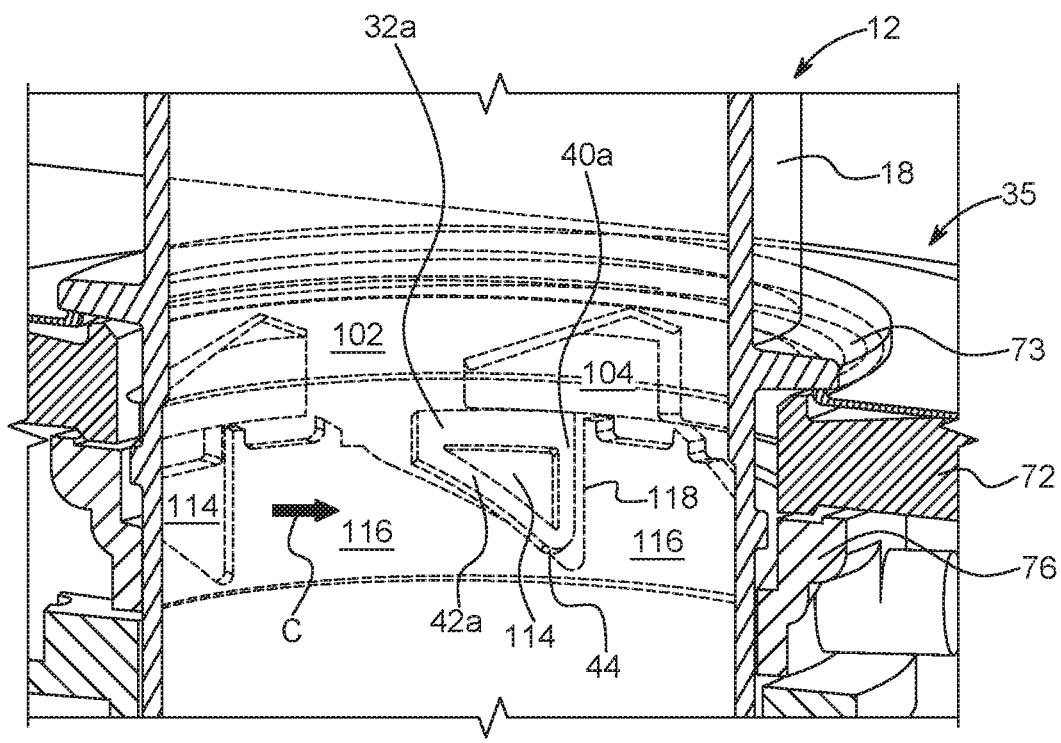
Figure 7H:
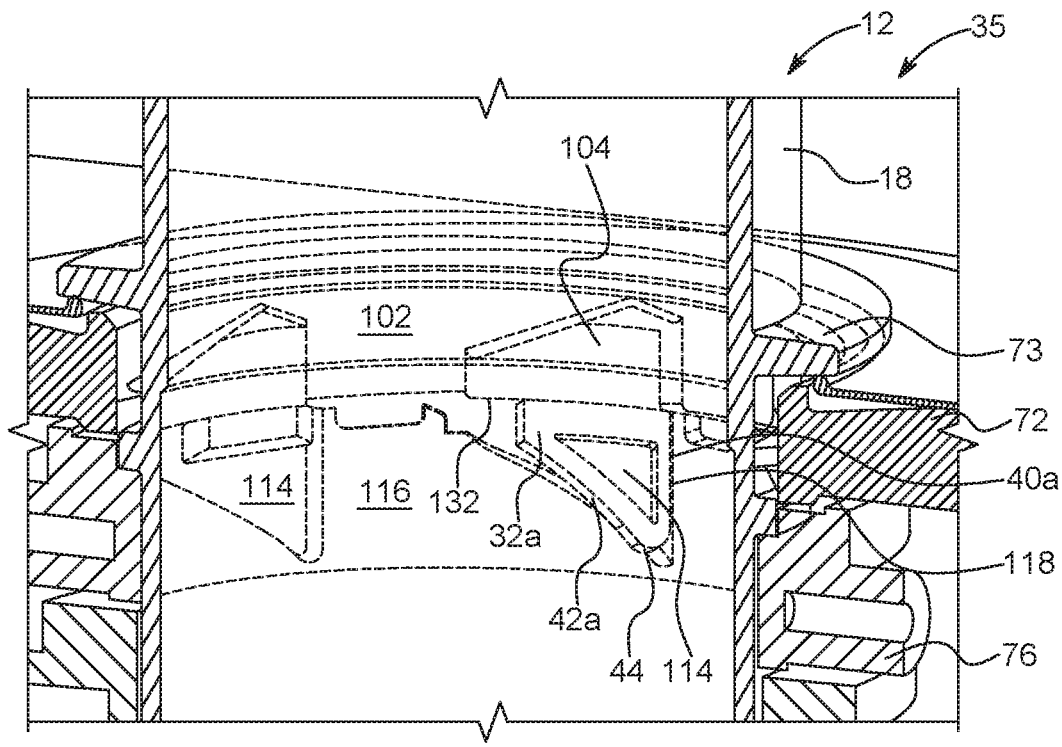

Continued movement of the syringe 12 in the proximal direction causes the locking ring 76 to rotate in the direction of arrow B, thereby allowing the first syringe retaining member 32a to move from the first recess 102 to the second recess 114. As the apex 44 and/or the guide surface 42a of the first syringe retaining member 32a moves along the ramp surface 122 of the second guide member 116 of the locking ring 76, the syringe 12 is inserted proximally into the syringe port 16 until the apex 44 of the first syringe retaining member 32a engages the bottom of the ramp surface 122 (FIG. 7F). In this position, the side surface 40a of the first syringe retaining member 32a may contact the stop surface 118. Upon release of the proximally directed force on the syringe barrel 18, the biasing mechanism 88 (shown in FIG. 5) urges the locking ring 76 in a direction of arrow C toward the first position of the locking ring 76. During this movement, the top surface 38a of the first syringe retaining member 32a is positioned proximally of a bottom surface 132 of the first guide member 104. When the locking ring 76 returns to its first position, the first syringe retaining member 32a is positioned within the second recess 114, with the top surface 38a of the first syringe retaining member 32a being positioned proximally from the bottom surface 132 of the first guide member 104, and the side surface 40a of the first syringe retaining member 32a being adjacent to the stop surface 118 of the second guide member 116 (FIG. 7G). In this first position, the syringe 12 is locked with the locking mechanism 35 which prevents withdrawal of the syringe barrel 18 from the syringe port 16. In some examples, the locking ring 76 may rotate the syringe barrel 18 by about 30° to lock the syringe 12 with the locking mechanism 35.

Figure 8A:
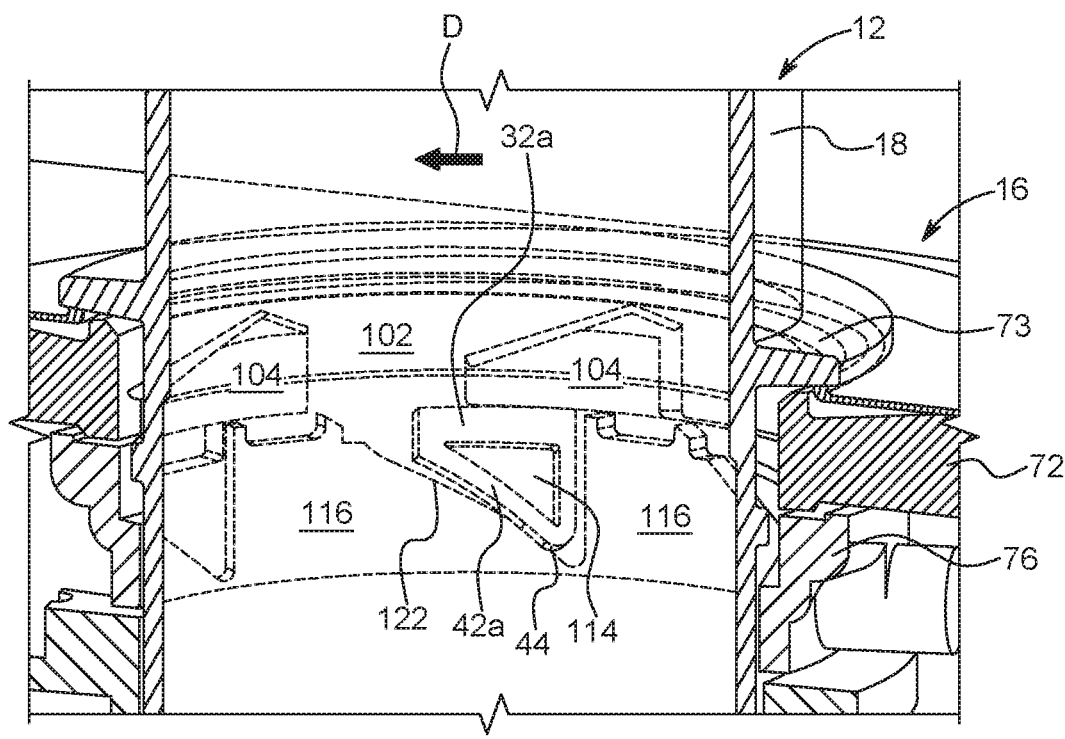
FIGS. 8A-8D are partially-transparent perspective views of the locking mechanism and the syringe showing movement of components of the locking mechanism during disengagement of the syringe from the locking mechanism.
Figure 8B:
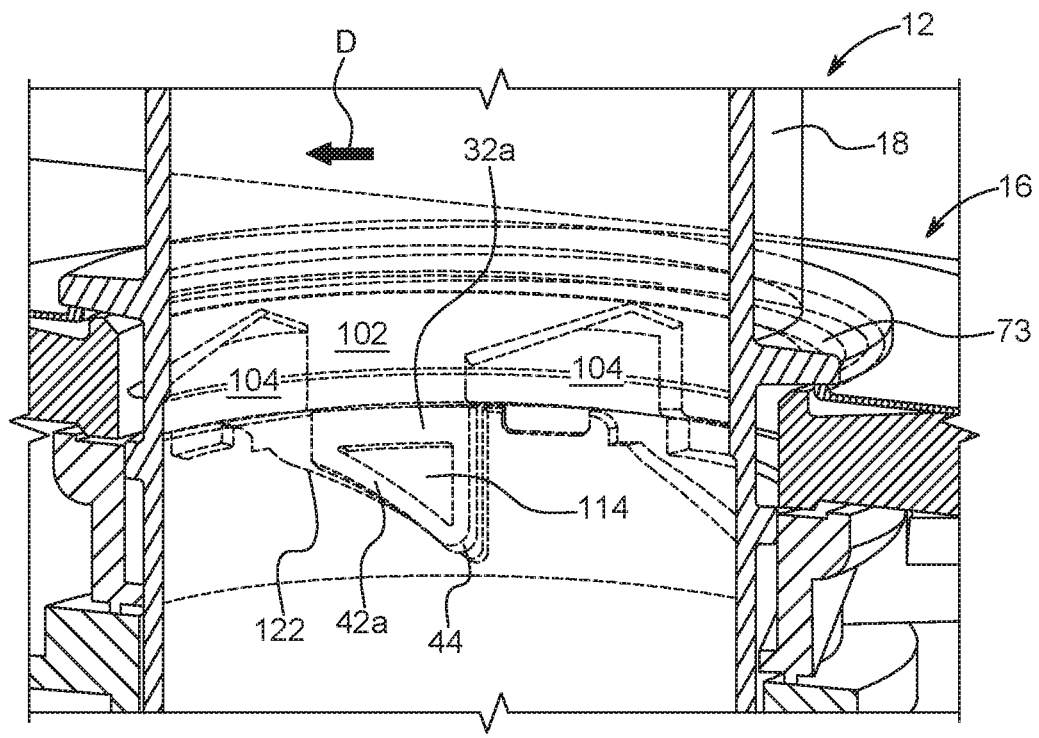
Figure 8C:
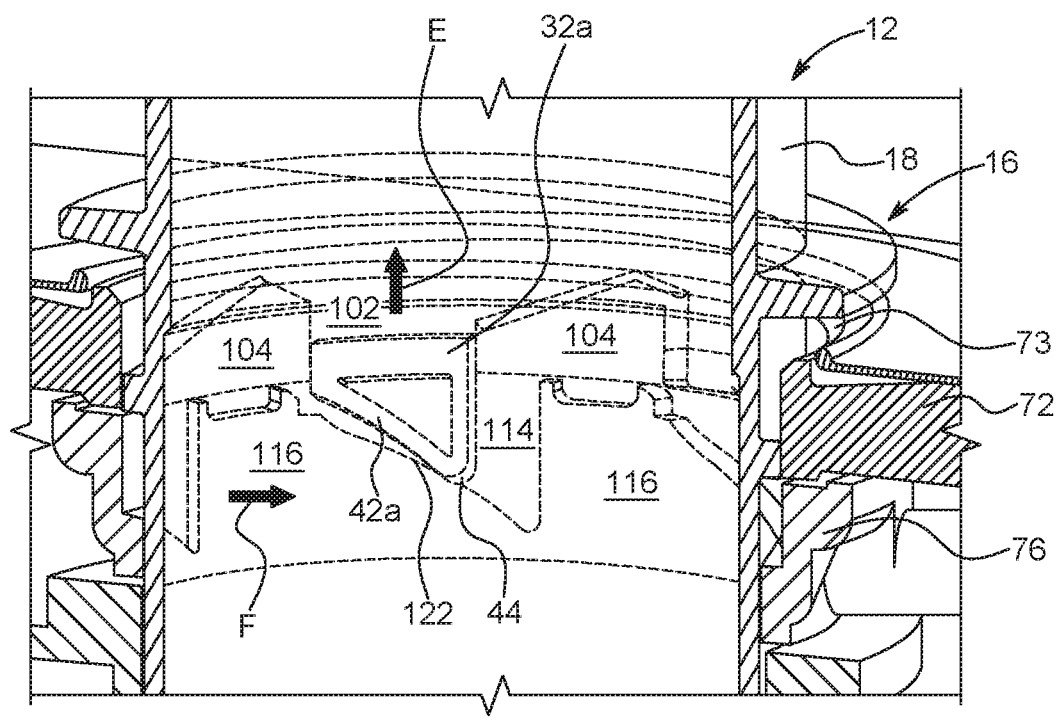
Figure 8D:
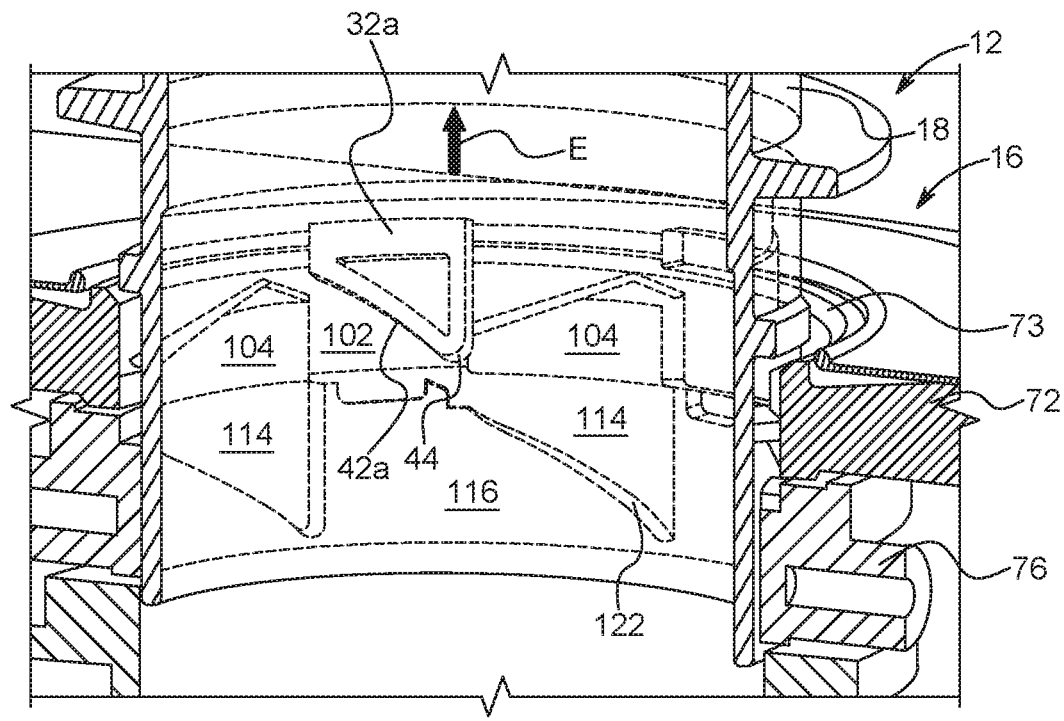

To unlock the syringe 12 from the syringe port 16, the syringe barrel 18 is rotated in a direction of arrow D around the longitudinal axis 15, as shown in FIG. 8A. The rotational movement of the syringe barrel 18 counters the restoring force of the biasing mechanism 88 (shown in FIG. 5). During the rotational movement of the syringe barrel 18 in the direction of arrow D, the apex 44 and/or the guide surface 42a of the first syringe retaining member 32a moves distally along the ramp surface 122 of the second guide member 116 as soon as the base surface 38a of the first syringe retaining member 32a clears the bottom surface 132 of the first guide member 104 (FIG. 8B). The syringe barrel 18 is ejected in a direction of arrow E shown in FIG. 8C due to interaction of the apex 44 and/or the guide surface 42a of the first syringe retaining member 32a with the ramp surface 122 of the second guide member 116. The syringe barrel 18 continues to move distally in the direction of arrow E due to a distal normal force component of the restoring force of the biasing mechanism 88 and axial guidance and syringe rotation prevention during ejection provided by first guide member 104. The syringe barrel 18 self-ejects from the locking mechanism 35 in the distal direction when the syringe barrel 18 is rotated by a predetermined angular rotation, such as about 30° (FIG. 8C). As the syringe 12 is ejected from its engagement with the locking ring 76 and removed from the syringe port 16, the restoring force of the biasing mechanism 88 (shown in FIG. 5) causes the locking ring 76 to return to its first position by rotating in a direction E shown in FIG. 8D in preparation for a subsequent insertion of a syringe 12.

Figure 9:
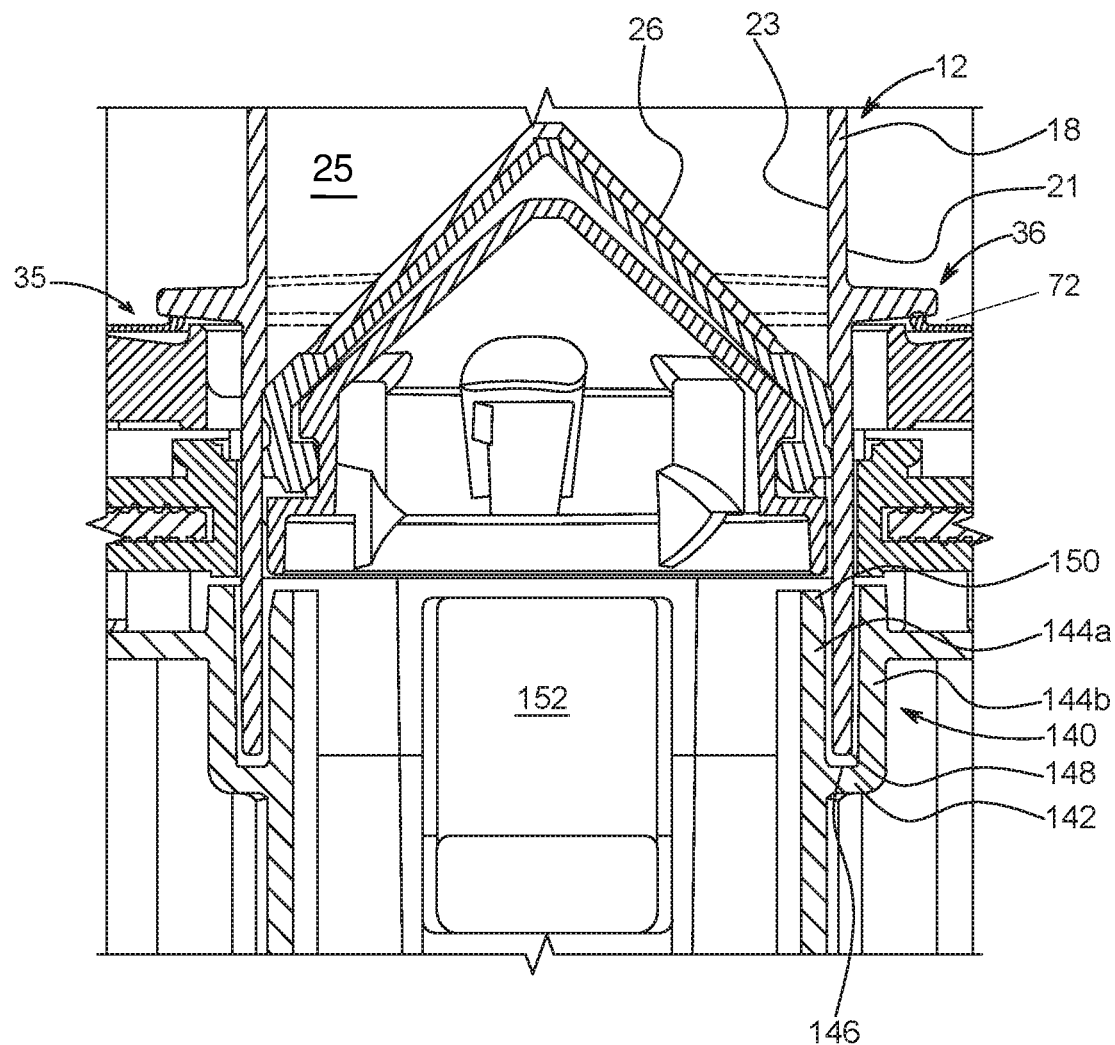
FIG. 9 is a side, cross-sectional view of an installed syringe and a fluid injector.

With reference to FIG. 9, the locking mechanism 35 may have a guard 140 configured to limit movement of the syringe barrel 18 and/or the plunger 26. For example, the guard 140 may limit the movement of the syringe barrel 18 in the proximal direction during insertion of the syringe 12 in the syringe port 16. Alternatively, or in addition, the guard 140 may limit the movement of the syringe plunger 26 in the proximal direction when the plunger 26 is engaged with a piston (not shown) of the injector 10 (shown in FIG. 1). In some examples, the drip flange 36 may be used to limit the movement of the syringe barrel 18 during insertion as an alternative or additional mechanism to the guard 140. The drip flange 36 may engage the top surface of cover plate 72 when the syringe 12 is fully inserted in the syringe port 16.

With continued reference to FIG. 9, the guard 140 may have a cradle 142 configured for receiving at least a portion of the proximal end 20 of the syringe barrel 18. In some examples, the cradle 142 may extend around at least a portion of a circumference of the syringe barrel 18. The cradle 142 may have an inner sidewall 144a and an outer sidewall 144b that surround at least a portion of the inner surface 23 and the outer surface 21 of the syringe barrel 18, respectively. In some examples, a bottom surface 146 of the cradle 142 may contact a terminal surface 148 at the proximal end 20 of the syringe barrel 18 when the syringe 12 is fully inserted in the syringe port 16. A top surface 150 of the inner sidewall 144a of the cradle 142 is positioned to delimit the proximal movement of the plunger 26 within the syringe barrel 18. For example, the top surface 150 of the inner sidewall 144a may engage a bottom or proximal surface of the plunger 26 to prevent further movement of the plunger 26 in the proximal direction. In this manner, interference between the plunger 26 and a component 152 of the injector 10 that may be positioned within the proximal end 20 of the syringe barrel 18 is prevented.

Although the disclosure has been described in detail for the purpose of illustration based on what is currently considered to be the most practical and preferred examples, it is to be understood that such detail is solely for that purpose and that the disclosure is not limited to the disclosed examples, but, on the contrary, is intended to cover modifications and equivalent arrangements. For example, it is to be understood that the present disclosure contemplates that, to the extent possible, one or more features of any example can be combined with one or more features of any other example.

The invention claimed is:

1. A medical fluid injector comprising:
an injector housing;
at least one syringe port in the injector housing for receiving a proximal portion of a syringe; and
a locking mechanism associated with the at least one syringe port for releasably locking the syringe within the at least one syringe port by releasably engaging at least one syringe retaining member of the syringe, the locking mechanism comprising:
a locking ring rotatable between a first locked position and a second insertion/removal position for insertion or removal of the syringe from the locking mechanism;
a biasing mechanism for biasing the locking ring in the first locked position; and
at least one second guide member on the locking ring, the at least one second guide member having:
a ramp surface configured for interacting with the at least one syringe retaining member of the syringe to rotate the locking ring from the first locked position to the second insertion/removal position as the syringe is inserted into the at least one syringe port, and
a top surface at a distal end of the ramp surface, the top surface having a first catch and a second catch each protruding distally from the top surface and separated from each other along the top surface,
wherein the second catch has a sloped portion angled in a direction toward the ramp surface.

2. The medical fluid injector of claim 1, wherein the at least one second guide member on the locking ring interacts with the at least one syringe retaining member of the syringe to rotate the locking ring from the first locked position to the second insertion/removal position when the syringe is rotated while in a syringe locked position in the locking mechanism.

3. The medical fluid injector of claim 2, wherein the ramp surface of the at least one second guide member interacts with the at least one syringe retaining member of the syringe to axially eject the syringe from the syringe locked position when the locking ring is rotated into the second insertion/removal position.

4. The medical fluid injector of claim 1, wherein the locking ring further comprises a stop surface at least partially extending from a proximal end of the ramp surface to a distal surface of the locking ring, wherein the stop surface prevents rotation of the syringe relative to the locking mechanism when the syringe is locked within the locking mechanism.

5. The medical fluid injector of claim 1, wherein the at least one syringe port further comprises a sidewall having a plurality of recesses and at least one first guide member extending radially inward from the sidewall and positioned between each adjacent recess of the plurality of recesses.

6. The medical fluid injector of claim 5, wherein the at least one first guide member comprises one or more guiding surfaces for guiding the at least one syringe retaining member into self-orienting alignment with the locking ring.

7. The medical fluid injector of claim 5, wherein the at least one first guide member comprises a first guiding ramp and a second guiding ramp, wherein the first guiding ramp and the second guiding ramp are inclined toward a first adjacent recess and a second adjacent recess, respectively, on each side of the at least one first guide member.

8. The medical fluid injector of claim 5, wherein the at least one first guide member has a proximal surface for abutting against a base surface of the at least one syringe retaining member when the syringe is locked within the locking mechanism to prevent distal movement of the syringe when locked in the locking mechanism.

9. The medical fluid injector of claim 1, wherein the biasing mechanism is a spring.

10. The medical fluid injector of claim 1, wherein the locking mechanism further comprises at least one sensor for detecting an angular position of the locking ring based on an orientation of a sensor pickup on the locking ring relative to the at least one sensor.

11. The medical fluid injector of claim 10, wherein the at least one sensor is an optical sensor, a Hall Effect sensor, or a combination thereof.

12. The medical fluid injector of claim 10, wherein the sensor pickup is a magnet.

13. The medical fluid injector of claim 1, wherein the at least one syringe port comprises a barcode reader system for reading at least one identification tag on the proximal portion of the syringe.

14. A fluid injector comprising an injector housing with at least one syringe port for receiving a syringe, the injector housing comprising:
- a locking mechanism associated with the at least one syringe port for securing the syringe within the at least one syringe port, wherein the locking mechanism is configured for engaging at least one syringe retaining member of the syringe to releasably lock the syringe within the at least one syringe port,
wherein the at least one syringe retaining member rotationally guides the syringe into self-orienting alignment with the locking mechanism and axially ejects the syringe from the locking mechanism upon rotation of the syringe, and
wherein the locking mechanism comprises:
- a locking ring disposed within the injector housing, the locking ring rotatable between a first locked position and a second insertion/removal position with rotation of the syringe about a longitudinal axis, the locking ring having a ramp surface configured for interacting with the at least one syringe retaining member of the syringe to rotate the locking ring from the first locked position to the second insertion/removal position, a top surface at a distal end of the ramp surface, the top surface having a first catch and a second catch each protruding distally from the top surface and separated from each other along the top surface, wherein the second catch has a sloped portion.

15. The fluid injector of claim 14, wherein the locking mechanism comprises:
- a housing having a central opening configured to receive a proximal end of the syringe; and
- a biasing mechanism for biasing the locking ring in the first locked position.

16. The fluid injector of claim 15, wherein the biasing mechanism is a spring.

17. The fluid injector of claim 15, wherein the locking mechanism further comprises at least one sensor for detecting an angular position of the locking ring based on orientation of a sensor pickup on the locking ring relative to the at least one sensor.

18. The fluid injector of claim 17, wherein the at least one sensor is an optical sensor, a Hall Effect sensor, or a combination thereof.

19. The fluid injector of claim 14, wherein the at least one syringe port further comprises a sidewall having a plurality of recesses and at least one first guide member positioned between each adjacent recess of the plurality of recesses.

20. The fluid injector of claim 19, wherein the at least one first guide member comprises one or more guiding surfaces for guiding the at least one syringe retaining member into self-orienting alignment with the locking ring.

* * * * *

UNITED STATES PATENT AND TRADEMARK OFFICE
CERTIFICATE OF CORRECTION

| | | |
|---|---|---|
| PATENT NO. | : 11,191,893 B2 | Page 1 of 1 |
| APPLICATION NO. | : 16/253539 | |
| DATED | : December 7, 2021 | |
| INVENTOR(S) | : Capone et al. | |

It is certified that error appears in the above-identified patent and that said Letters Patent is hereby corrected as shown below:

In the Specification

In Column 9, Lines 13-15, delete "first syringe retaining members 32 are provided, the first syringe retaining members 32" and insert -- first syringe retaining members 32a are provided, the first syringe retaining members 32a --, therefor.

In Column 10, Line 40, delete "first retaining member 32a" and insert -- first syringe retaining member 32a --, therefor.

In Column 10, Lines 53-54, delete "first retaining member 32a" and insert -- first syringe retaining member 32a --, therefor.

In Column 11, Line 24, delete "outer surface 18" and insert -- outer surface 21 --, therefor.

In Column 12, Line 12, delete "connection interface 100." and insert -- connection interface. --, therefor.

In Column 12, Lines 15-16, delete "cover 72" and insert -- cover plate 72 --, therefor.

In Column 14, Line 4, delete "The sensor 81" and insert -- The --, therefor.

In Column 16, Line 12, delete "locking mechanism 12." and insert -- locking mechanism 35. --, therefor.

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*